(12) United States Patent
Kitagawa et al.

(10) Patent No.: US 8,438,896 B2
(45) Date of Patent: May 14, 2013

(54) ENDOSCOPIC INSERTION PORTION AND MANUFACTURING METHOD THEREOF

(75) Inventors: Hideya Kitagawa, Hachioji (JP); Shunichi Imai, Okaya (JP)

(73) Assignee: Olympus Corporation, Tokyo (JP)

( * ) Notice: Subject to any disclaimer, the term of this patent is extended or adjusted under 35 U.S.C. 154(b) by 280 days.

(21) Appl. No.: 12/908,415

(22) Filed: Oct. 20, 2010

(65) Prior Publication Data
US 2011/0030194 A1 Feb. 10, 2011

Related U.S. Application Data

(62) Division of application No. 11/658,815, filed as application No. PCT/JP2006/317108 on Aug. 30, 2006, now abandoned.

(30) Foreign Application Priority Data

Dec. 9, 2005 (JP) ................................. 2005-356372
Jan. 12, 2006 (JP) ................................. 2006-005231

(51) Int. Cl.
*B21J 11/00* (2006.01)

(52) U.S. Cl.
USPC ............................................ 72/404; 72/335

(58) Field of Classification Search .................. 600/139, 600/141, 142; 72/367.1, 368, 379.2, 404, 72/405.01, 331, 335
See application file for complete search history.

(56) References Cited

U.S. PATENT DOCUMENTS

| | | | |
|---|---|---|---|
| 5,178,129 A | | 1/1993 | Chikama et al. |
| 5,927,920 A | * | 7/1999 | Swanstrom .................... 411/180 |
| 6,079,922 A | * | 6/2000 | Ross et al. ..................... 411/180 |
| 6,202,465 B1 | * | 3/2001 | Jankoski et al. ................. 72/368 |
| 6,439,819 B2 | * | 8/2002 | Swanstrom et al. ........... 411/437 |
| 7,171,839 B2 | * | 2/2007 | Krzyzanowski ............. 72/379.2 |
| 7,374,495 B2 | * | 5/2008 | Ball ................................ 470/25 |
| 2003/0083622 A1 | | 5/2003 | Osawa et al. |
| 2005/0131279 A1 | | 6/2005 | Boulais et al. |

FOREIGN PATENT DOCUMENTS

| | | |
|---|---|---|
| JP | 55-154001 U | 11/1980 |
| JP | 61-21042 Y2 | 6/1986 |
| JP | 3-202040 A | 9/1991 |
| JP | 3-104301 U | 10/1991 |
| JP | 7-128599 A | 5/1995 |
| JP | 9-299317 A | 11/1997 |

OTHER PUBLICATIONS

International Preliminary Report on Patentability and Written Opinion of the International Searching Authority dated Jun. 19, 2008, issued in counterpart International Application PCT/JP2006/317108.

* cited by examiner

*Primary Examiner* — Edward Tolan
(74) *Attorney, Agent, or Firm* — Holtz, Holtz, Goodman & Chick, P.C.

(57) ABSTRACT

A method of manufacturing an endoscopic insertion portion with high manufacturing efficiency is provided. The endoscopic insertion portion includes a plurality of bending parts provided side by side with each other, a protruding portion provided in one of each two adjacent ones of the bending parts, and a receiving portion provided in the other of each two adjacent ones of the bending parts and into which the protruding portion is inserted rotatably. The method includes forming, in at least one plate material, a first bending part preparation portion for the formation of the one bending part and a second bending part preparation portion for the formation of the other bending part, connecting the first bending part preparation portion and the second bending part preparation portion by press processing, and forming the first and second bending part preparation portion into a cylindrical shape by press processing.

12 Claims, 16 Drawing Sheets

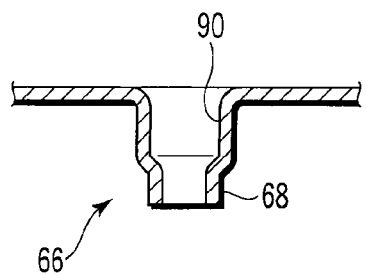
F I G. 4E
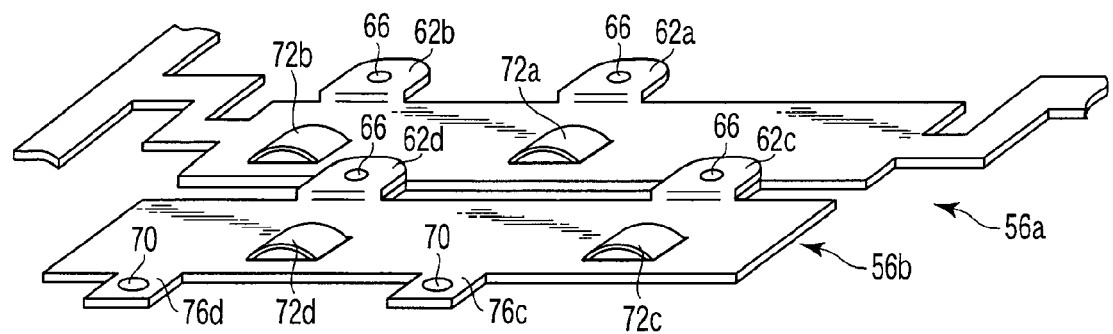
F I G. 5

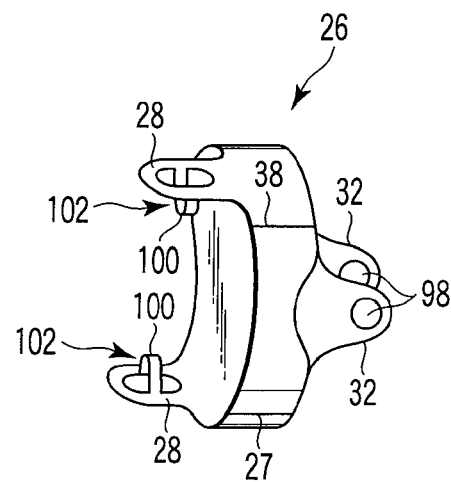
F I G. 8A
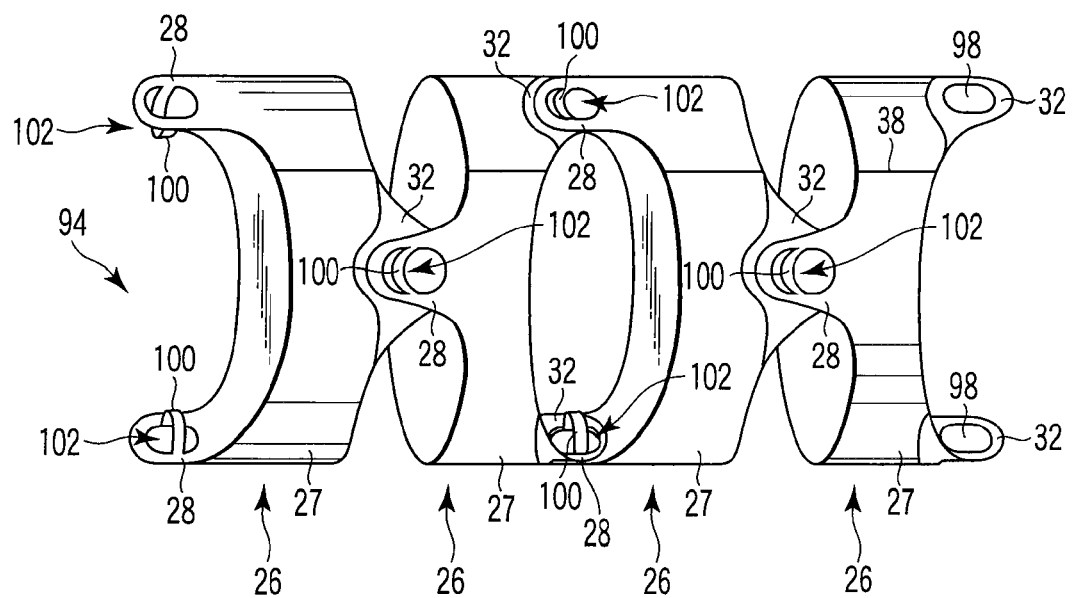
F I G. 8B

ENDOSCOPIC INSERTION PORTION AND MANUFACTURING METHOD THEREOF

This is a Divisional Application of U.S. application Ser. No. 11/658,815, filed Jan. 30, 2007 now abandoned, which is a U.S. National Phase Application under 35 USC 371 of International Application PCT/JP2006/317108, filed Aug. 30, 2006, the entire contents of both of which are incorporated herein by reference.

TECHNICAL FIELD

The present invention relates to an endoscopic insertion portion having a bending portion which is operated to bend, and to a manufacturing method thereof.

BACKGROUND ART

A bending portion which is operated to bend is provided in an insertion portion of an endoscope. In a bending tube of this bending portion, a plurality of cylindrical bending parts are coaxially provided side by side with each other, and the adjacent two bending parts are swingably coupled by a pair of coupling portions located symmetrically with respect to a central axis. For example, tongue piece portions are provided to protrude on both end faces of the bending part, and the tongue piece portions of the adjacent bending parts are made to overlap one other and then rotatably riveted to each another, thereby forming the coupling portions.

Jpn. Pat. Appln. KOKAI Publication No. 7-128599 has disclosed that, in order to improve the assemblability of the bending tube, a steel ball is interposed between the two tongue piece portions overlapping one another instead of being riveted, thereby forming a coupling portion.

DISCLOSURE OF INVENTION

However, in conventional bending tubes, it is necessary to assemble minute precision components with extremely high accuracy even in the case of the bending tube as in Jpn. Pat. Appln. KOKAI Publication No. 7-128599. Thus, in the manufacture of the bending tube, it is necessary to depend on highly skilled manual workers or to have a large-scale high-performance automatic assembling device, which makes it difficult to improve the efficiency of manufacturing the endoscopic insertion portion.

The present invention has been made in view of the foregoing problem, and is directed to provide a method of manufacturing an endoscopic insertion portion with high manufacturing efficiency, and an endoscopic insertion portion capable of improving the manufacturing efficiency.

According to an aspect of the present invention, a method of manufacturing an endoscopic insertion portion which includes a plurality of bending parts provided side by side with each other, a protruding portion provided in one of the adjacent two bending parts, and a receiving portion which are provided in the other of the two bending parts and into which the protruding portion are inserted rotatably so that the two bending parts swing with respect to each other, the method is characterized by comprising: forming, in one plate material or a plurality of plate materials, a first bending part preparation portion for the formation of the one bending part and a second bending part preparation portion for the formation of the other bending part; connecting the first bending part preparation portion and the second bending part preparation portion by press processing; and forming the first and second bending part preparation portion into a cylindrical shape by press processing.

According to a preferred aspect of the present invention, the method of manufacturing an endoscopic insertion portion is characterized in that the forming the first bending part preparation portion and the second bending part preparation portion includes: forming a protruding portion preparation portion for the formation of the protruding portion in the plate material by press processing; forming a receiving portion preparation portion for the formation of the receiving portion in the plate material by press processing; forming the first bending part preparation portion having the protruding portion preparation portion in the plate material by punching processing; and forming the second bending part preparation portion having the receiving portion preparation portion in the plate material by punching processing, the connecting the first bending part preparation portion and the second bending part preparation portion by press processing includes: aligning the protruding portion preparation portion with the receiving portion preparation portion in a direction vertical to the plate material by moving one of the first and second bending part preparation portion by Z-shape bending processing; and inserting the protruding portion preparation portion into the receiving portion preparation portion rotatably by subjecting one of the first and second bending part preparation portion to dropping processing, and the forming the first and second bending part preparation portion into the cylindrical shape by press processing includes: subjecting the first and second bending part preparation portion to U-shape bending processing at least one time to form the first and second bending part preparation portion into the cylindrical shape; and subjecting the first and second bending part preparation portion which have undergone the U-shape bending processing to O-shape bending processing to form the first and second bending part preparation portion into the cylindrical shape.

According to a preferred aspect of the present invention, the method of manufacturing an endoscopic insertion portion is characterized in that in order to simultaneously process the first and second bending part preparation portion at processing positions for the implementation of the above steps, the plate material is passed on to the processing positions for the implementation of the steps in the order of: the forming the protruding portion preparation portion by press processing; the forming the receiving portion preparation portion by press processing; the forming the first bending part preparation portion by punching processing; the forming the second bending part preparation portion by punching processing; the aligning; the inserting; the subjecting to the U-shape bending processing; and the subjecting to the O-shape bending processing.

According to a preferred aspect of the present invention, the method of manufacturing an endoscopic insertion portion is characterized by further comprising: joining both ends of the first and second bending part preparation portion which abut against each other due to the O-shape bending processing.

According to a preferred aspect of the present invention, the method of manufacturing an endoscopic insertion portion is characterized in that the bending part has a wire receiving portion through which a wire is inserted, the manufacturing method further comprising forming a wire receiving portion preparation portion for the formation of the wire receiving portion by slit processing and bending processing for the plate material.

According to a preferred aspect of the present invention, the method of manufacturing an endoscopic insertion portion is characterized in that the bending part has a wire receiving portion through which a wire is inserted, the manufacturing method further comprising forming a wire receiving portion preparation portion for the formation of the wire receiving portion by punching processing and folding processing for the plate material.

According to a preferred aspect of the present invention, the method of manufacturing an endoscopic insertion portion is characterized in that the receiving portion includes a through hole through which the protruding portion is inserted; the forming the first bending part preparation portion and the second bending part preparation portion includes: forming a protruding portion preparation portion for the formation of the protruding portion in a first plate-shaped portion by press processing; forming, in the protruding portion preparation portion by press processing, insertion hole preparation portion for the formation of insertion hole through which an operation wire for a bending operation of the endoscopic insertion portion is inserted; forming through hole preparation portion for the formation of the through hole in a second plate-shaped portion by press processing; forming the first bending part preparation portion having the protruding portion preparation portion in the first plate-shaped portion by punching processing; and forming the second bending part preparation portion having the through hole preparation portion in the second plate-shaped portion by punching processing, the connecting the first bending part preparation portion and the second bending part preparation portion by press processing includes: aligning the protruding portion preparation portion with the through hole preparation portion by relatively moving the first and second bending part preparation portion; and connecting the first and second bending part preparation portion to each other by inserting the protruding portion preparation portion into the through hole preparation portion rotatably, and the forming the first and second bending part preparation portion into the cylindrical shape by press processing includes: subjecting the first and second bending part preparation portion to U-shape bending processing at least one time to form the first and second bending part preparation portion connected to each other into the cylindrical shape; and subjecting the first and second bending part preparation portion which have undergone the U-shape bending processing to O-shape bending processing to form the first and second bending part preparation portion connected to each other into the cylindrical shape.

According to a preferred aspect of the present invention, the method of manufacturing an endoscopic insertion portion is characterized in that the first plate-shaped portion and the second plate-shaped portion are parts of the same plate material; the aligning includes aligning the protruding portion preparation portion with the through hole preparation portion in a direction vertical to the plate material by moving one of the first and second bending part preparation portion by Z-shape bending processing; and the connecting by the inserting includes connecting the first and second bending part preparation portion to each other by subjecting one of the -first and second bending part preparation portion to dropping processing to insert the protruding portion preparation portion into the through hole preparation portion rotatably.

According to a preferred aspect of the present invention, the method of manufacturing an endoscopic insertion portion is characterized in that in order to simultaneously process the first and second bending part preparation portion at processing positions for the implementation of the above steps, the plate material is passed on to the processing positions for the implementation of the steps in the order of: the forming the protruding portion preparation portion by press processing; the forming the insertion hole preparation portion by press processing; the forming the through hole preparation portion by press processing; the forming the first bending part preparation portion by punching processing; the forming the second bending part preparation portion by punching processing; the aligning; the connecting by the inserting; the subjecting to the U-shape bending processing; and the subjecting to the O-shape bending processing.

According to a preferred aspect of the present invention, the method of manufacturing an endoscopic insertion portion is characterized in that the first plate-shaped portion and the second plate-shaped portion are a part of a first plate material and a part of a second plate material, respectively, and the connecting includes connecting one of the first and second bending part preparation portion of one of the first and second plate materials to the other of the first and second bending part preparation portion of the other of the first and second plate materials by separating the one of the first and second bending part preparation portion from the one of the first and second plate materials and then inserting the protruding portion preparation portion into the through hole preparation portion rotatably.

According to a preferred aspect of the present invention, the method of manufacturing an endoscopic insertion portion is characterized in that the first plate material is continuously processed by being passed on to the processing positions for the implementation of the steps in the order of: the forming the protruding portion preparation portion by press processing; and the forming the first bending part preparation portion by punching processing, the second plate material is continuously processed by being passed on to the processing positions for the implementation of the steps in the order of: the forming the through hole preparation portion by press processing; and the forming the second bending part preparation portion by punching processing, and the first or second plate material is continuously processed by being passed on to the processing positions for the implementation of the steps in the order of: the subjecting to the U-shape bending processing; and the subjecting to the O-shape bending processing.

According to another aspect of the present invention, an endoscopic insertion portion is characterized by comprising: a plurality of bending parts provided side by side with each other; a protruding portion integrally provided in one of the adjacent two bending parts; and a receiving portion which are integrally provided in the other of the two bending parts and into which the protruding portion are inserted rotatably so that the two bending parts swing with respect to each other, wherein the bending parts, the protruding portion and the receiving portion are formed in the following manner: forming, by press processing, a first bending part preparation portion for the formation of the one bending part and a second bending part preparation portion for the formation of the other bending part, connecting the first bending part preparation portion to the second bending part preparation portion, and forming the first and second bending part preparation portion into a cylindrical shape.

According to a preferred aspect of the present invention, the endoscopic insertion portion is characterized in that the bending parts, the protruding portion and the receiving portion are formed by a single plate material.

According to a preferred aspect of the present invention, the endoscopic insertion portion is characterized in that the bending parts, the protruding portion and the receiving portion form a bending tube forming a bending portion which is operated to bend and a flexible insertion tube.

According to a preferred aspect of the present invention, the endoscopic insertion portion is characterized in that the receiving portion includes a through hole through which the protruding portion is inserted, and the protruding portion is integrally provided in the one bending part by press processing, and has an insertion hole through which an operation wire for a bending operation of the endoscopic insertion portion is inserted.

According to a preferred aspect of the present invention, the endoscopic insertion portion is characterized in that the plurality of bending parts are bending parts of one kind, and a certain bending part has protruding portion for the through hole of the bending part provided side by side on one side of the certain bending part, and through hole for the protruding portion of the bending part provided side by side on the other side thereof.

According to a preferred aspect of the present invention, the endoscopic insertion portion is characterized in that the plurality of bending parts are bending parts of two kinds, a certain bending part has protruding portion for the through holes of two bending parts provided side by side on one and the other sides of the certain bending part, and a bending part provided side by side with the certain bending part has through holes for the protruding portion of two bending parts provided side by side on one and the other sides of the bending part provided side by side with the certain bending part.

According to another aspect of the present invention, an endoscope is characterized by comprising the above-mentioned endoscopic insertion portion.

According to the method of manufacturing the endoscopic insertion portion of the present invention, the manufacturing efficiency is increased.

Furthermore, according to the endoscopic insertion portion of the present invention, the efficiency of manufacturing the endoscopic insertion portion can be improved.

BRIEF DESCRIPTION OF DRAWINGS

FIG. 4E is a diagram for explaining the burring processing of the plate material in the method of manufacturing the endoscopic insertion portion in the first embodiment of the present invention;

FIG. 5 is a perspective view showing half-finished bending parts in the method of manufacturing the endoscopic insertion portion in the first embodiment of the present invention;

FIG. 8A is a perspective view showing a bending part of a bending tube of an endoscope in a fourth embodiment of the present invention;

FIG. 8B is a perspective view showing the bending tube of the endoscope in the fourth embodiment of the present invention;

BEST MODE FOR CARRYING OUT THE INVENTION

A first embodiment of the present invention will hereinafter be described in reference to FIG. 1 to FIG. 5.

Figure 1:
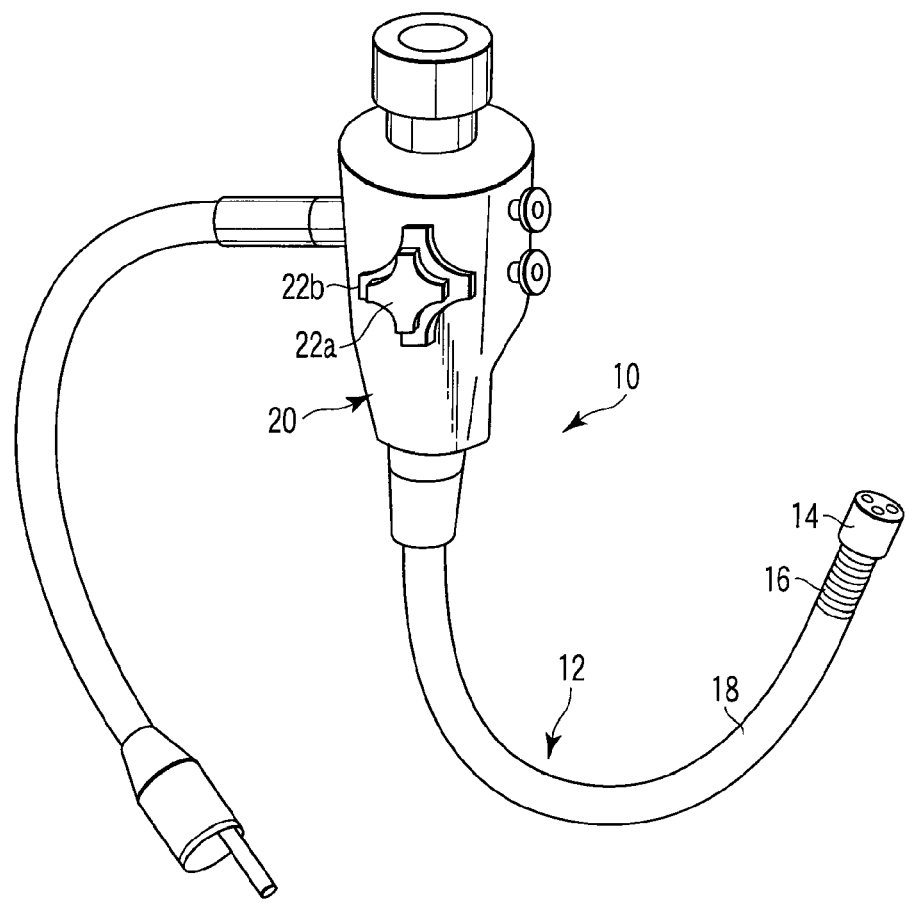
FIG. 1 is a perspective view showing an endoscope in a first embodiment of the present invention.

As shown in FIG. 1, an endoscope 10 in the present embodiment has an elongate insertion portion 12 to be inserted into a body cavity. This insertion portion 12 is formed by coupling, from a distal end side in order, a distal end forming portion 14, a bending portion 16 which is operated to bend, and a long and flexible insertion tube portion 18. An operation portion 20 which is held and operated by an operator is coupled to the proximal end of the insertion portion 12. The operation portion 20 is provided with a vertical bending operation knob 22a and a horizontal bending operation knob 22b for the bending operation of the bending, portion 16.

Figure 2:
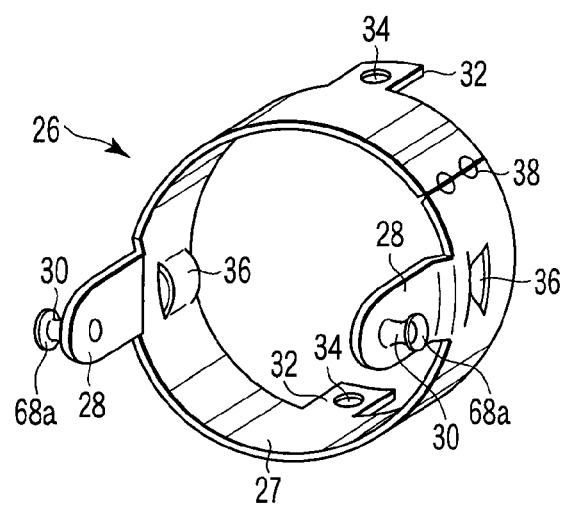
FIG. 2 is a perspective view showing a bending part of a bending tube of the endoscope in the first embodiment of the present invention.

Referring to FIG. 1 and FIG. 2, a bending tube forming the framework of the bending portion 16 is formed of a single plate material by press processing, as described later. In this bending tube, a plurality of thin and cylindrical bending parts 26 are coaxially coupled together and provided side by side. It is to be noted that one of the bending parts 26 that are provided side by side is shown in FIG. 2, and the bending parts preceding and following this bending part are not shown therein.

On one end face of the circumferential portion 27 of the bending part 26, a pair of protruding portion tongue piece portions 28 is provided to protrude in the direction of the central axis of the bending part 26 at positions symmetrical with respect to the central axis. Step corresponding to the thickness of the plate material are formed inwardly in the diametrical direction of the bending part 26 in connection portions between the circumferential portion 27 of the bending part 26 and the protruding portion tongue piece portions 28, and the protruding portion tongue piece portions 28 are arranged substantially parallel to the circumferential portion 27 inside the circumferential portion 27 in the diametrical direction thereof and serve as a minor diameter circumferential portion. Further, substantially cylindrical hinge protruding portions 30 are provided in a diametrically outwardly protruding manner on diametrically outer sides of the protruding portion tongue piece portions 28. On the other hand, on the other end face of the bending part 26, a pair of receiving portion tongue piece portions 32 is provided to protrude in the direction of the central axis of the bending part 26 at positions which are rotationally moved about 90° from the positions of the pair of protruding portion tongue piece portions 28 when viewed in the direction of the central axis of the bending part 26. These receiving portion tongue piece portions 32 are arranged substantially parallel to the circumferential portion 27 of the bending part 26, and have about the same diameter as that of the circumferential portion 27. Moreover, hinge holes 34 as receiving portions are diametrically passed through the receiving portion tongue piece portions 32.

Therefore, in the group of bending parts 26 coupled to each other and arranged side by side, the adjacent two bending parts 26 are arranged so that they are displaced about 90° from each other when viewed in the direction of the central axis of the bending portion 16. Further, the protruding portion tongue piece portions 28 and the receiving portion tongue piece portions 32 of the adjacent two bending parts 26 are made to overlap each other, and the hinge protruding portions 30 of the protruding portion tongue piece portions 28 are inserted rotatably in the hinge holes 34 of the receiving portion tongue piece portions 32. Here, the hinge protruding portions 30 are in a substantially cylindrical shape and the hinge holes 34 are in a substantially elliptic cylinder shape, and the outside diameter of the hinge protruding portions 30 substantially corresponds to the diameter of the minor axes of the hinge holes 34, and then the hinge protruding portions 30 are fitted into the hinge holes 34. Moreover, diameter expanded portions 68a for prevention of the drop from the hinge holes 34 are formed at protruding ends of the hinge protruding portions 30.

The pair of hinge protruding portions 30 is rotated in the pair of hinge holes 34, between the adjacent two bending parts 26, such that these two bending parts 26 swing with respect to each other. Further, the direction in which the bending part 26 on the front end side of a certain bending part 26 swings with respect to the certain bending part 26 is substantially perpendicular to the direction in which the bending part 26 on the rear end side of the certain bending part 26 swings with respect to the certain bending part 26, and the combination of such swings of the bending parts 26 enables the bending tube to bend in any direction.

Furthermore, a pair of wire receiving portions 36 through which operation wires for the bending operation of the bending portion 16 are inserted is formed in each of the bending parts 26. These wire receiving portions 36 have a form in which parts between circumferential slits provided side by side in each of the bending parts 26 protrude in V shape inwardly in the diametrical direction of the bending part 26. Moreover, the pairs of wire receiving portions 36 of the bending parts 26 are arranged so that these pairs are formed in alternate positions in the axial direction of the bending portion 16 sequentially with respect to an observation field of the endoscope 10, for example, at vertical positions, at horizontal positions, at vertical positions, at horizontal positions, and so on. In the present embodiment, the pair of wire receiving portions 36 is provided side by side with the protruding portion tongue piece portions 28 of the bending part 26 in the axial direction of the bending portion 16. The operation wires for vertical and horizontal bending operations are inserted through the respective wire receiving portions 36 at the vertical and horizontal positions, so that the bending portion 16 can be operated to bend in vertical and horizontal directions.

It is to be noted that, as described later in detail, the bending part 26 is formed by deforming a long plate-shaped bending part preparation portion 56a, 56b (see FIG. 4A to FIG. 4D) into a cylindrical shape, and joining, in a spot shape by laser welding and others, two portions in an abutting part where the two end faces at both ends of the bending part preparation portion abut against each other. Alternatively, one portion in the abutting part may be joined in the spot shape by the laser welding and others, or the abutting part may be joined by the laser welding and others to form a junction 38 over the entire length of the bending part 26 in the axial direction of the bending portion 16.

Next, a method of manufacturing the endoscopic insertion portion 12 in the present embodiment will be described.

Figure 3:
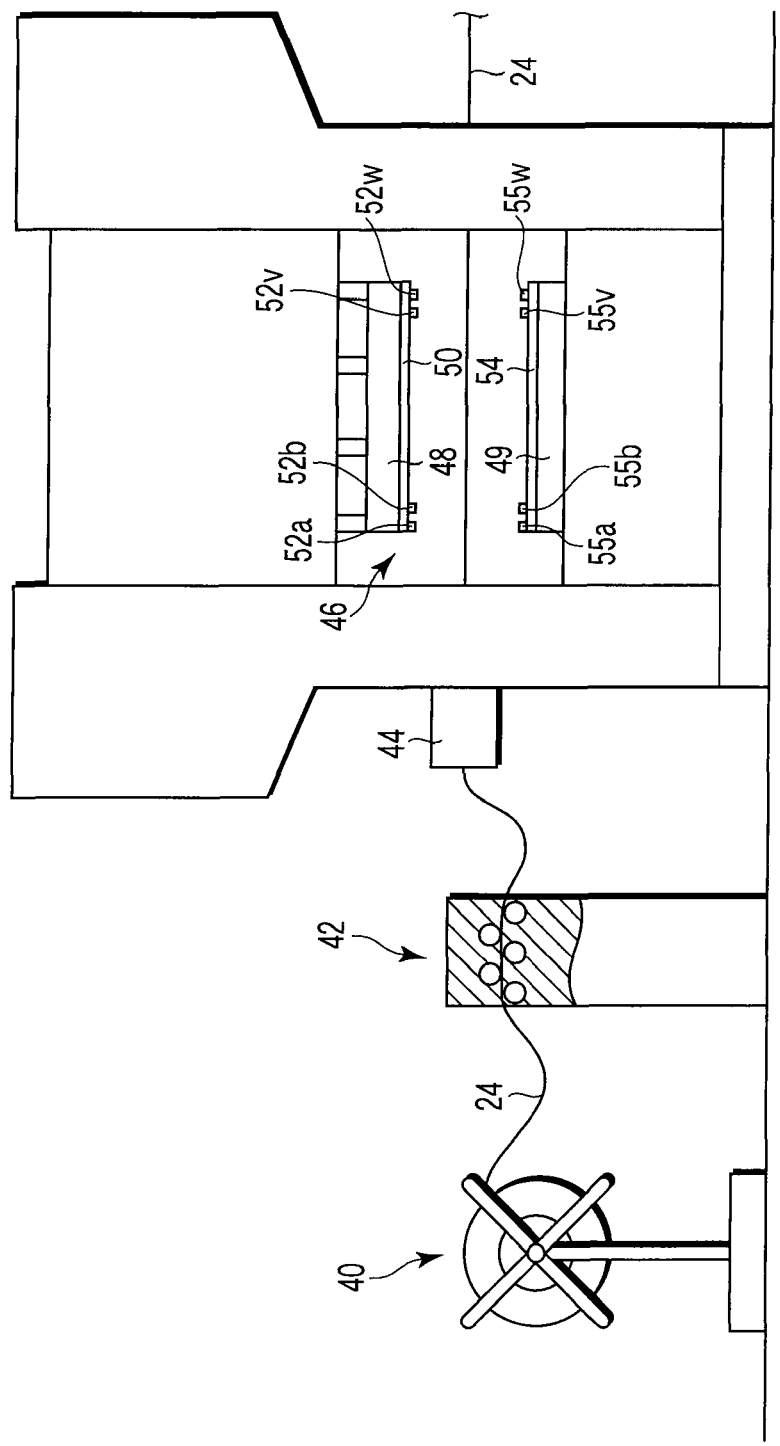
FIG. 3 is a schematic diagram showing a pressing machine used in a method of manufacturing an endoscopic insertion portion in the first embodiment of the present invention.
Figure 4A:
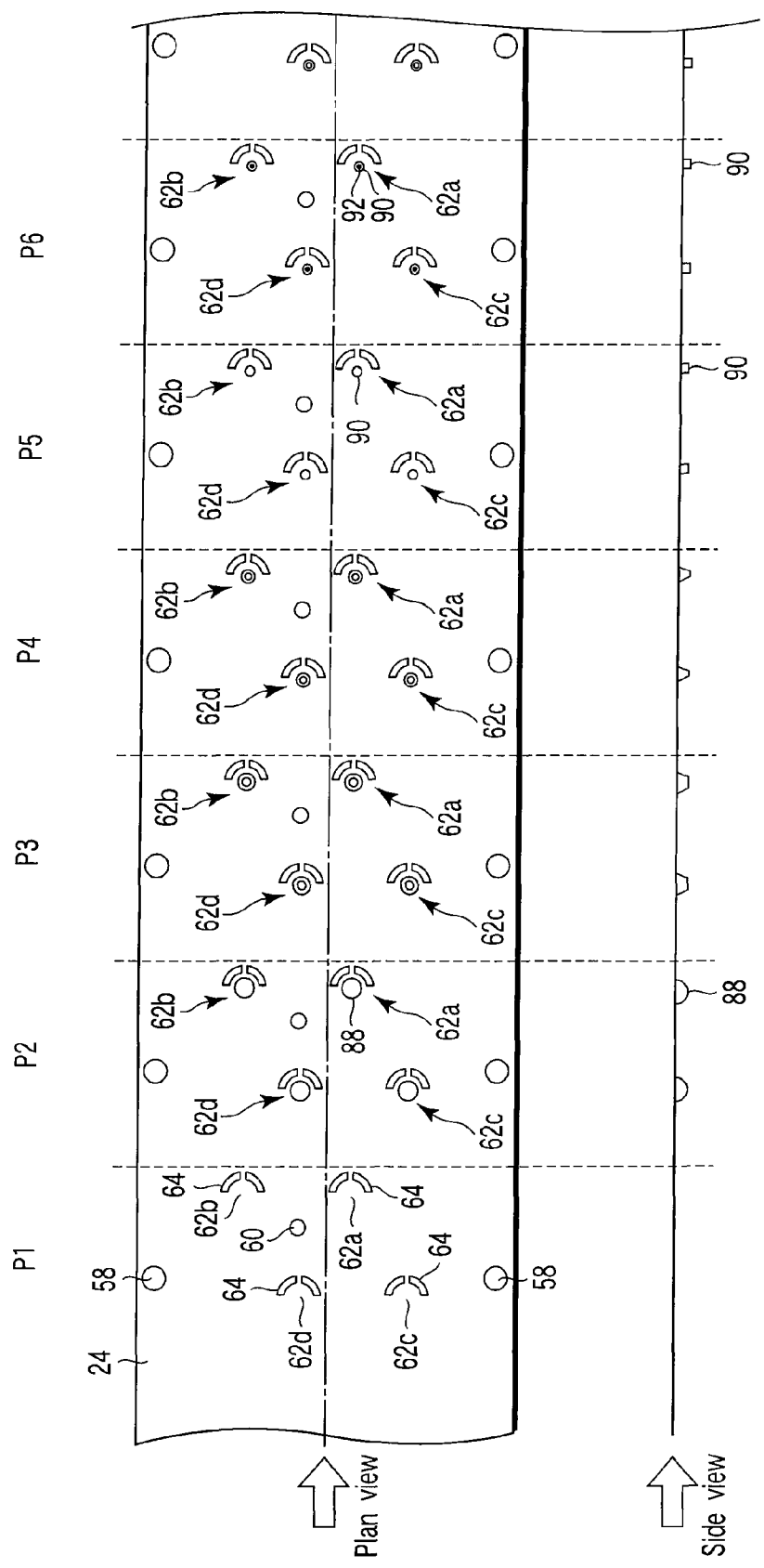
FIG. 4A is a first diagram for explaining the press processing of a plate material in the method of manufacturing the endoscopic insertion portion in the first embodiment of the present invention.
Figure 4B:
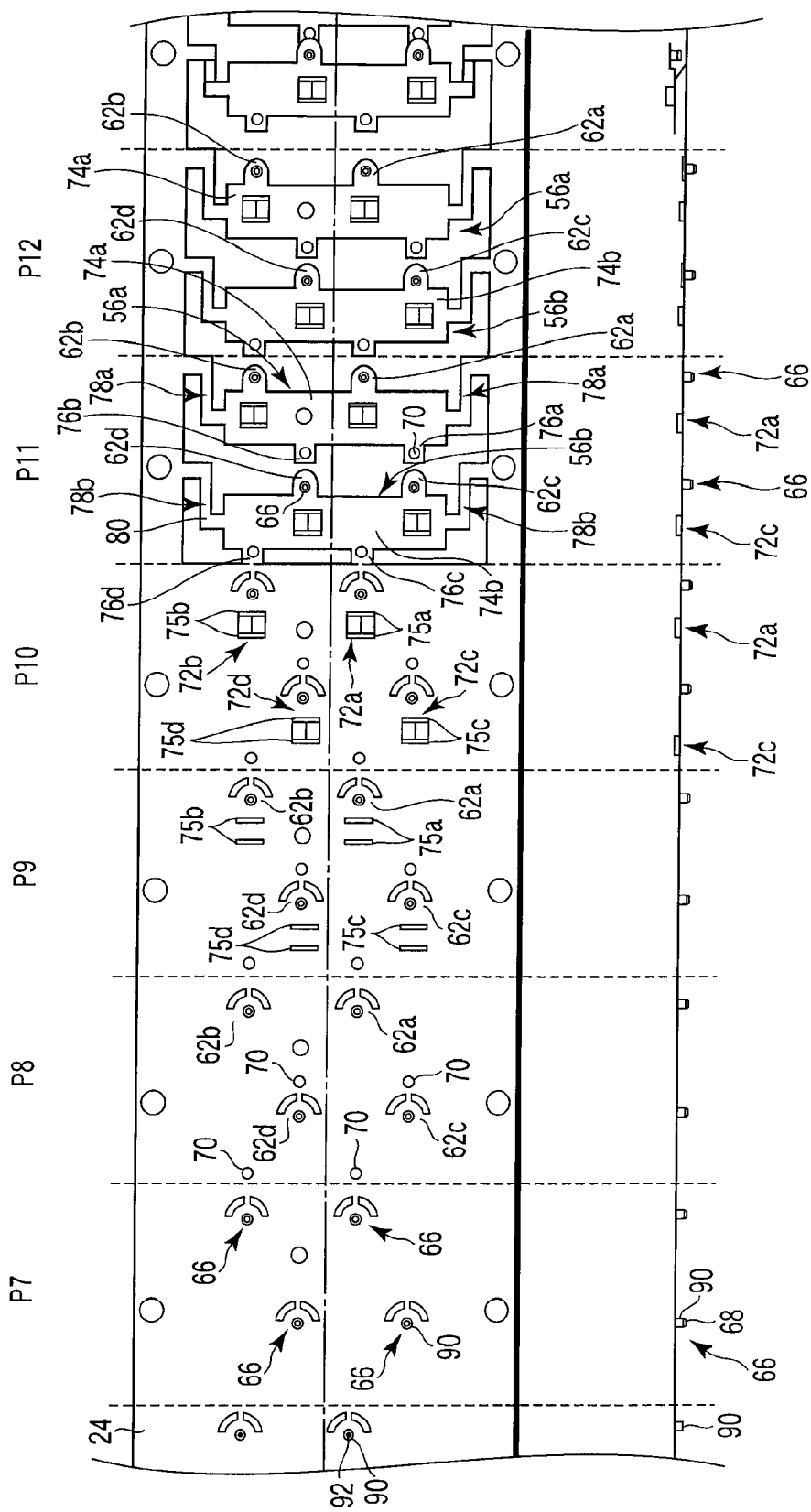
FIG. 4B is a second diagram for explaining the press processing of the plate material in the method of manufacturing the endoscopic insertion portion in the first embodiment of the present invention.
Figure 4C:
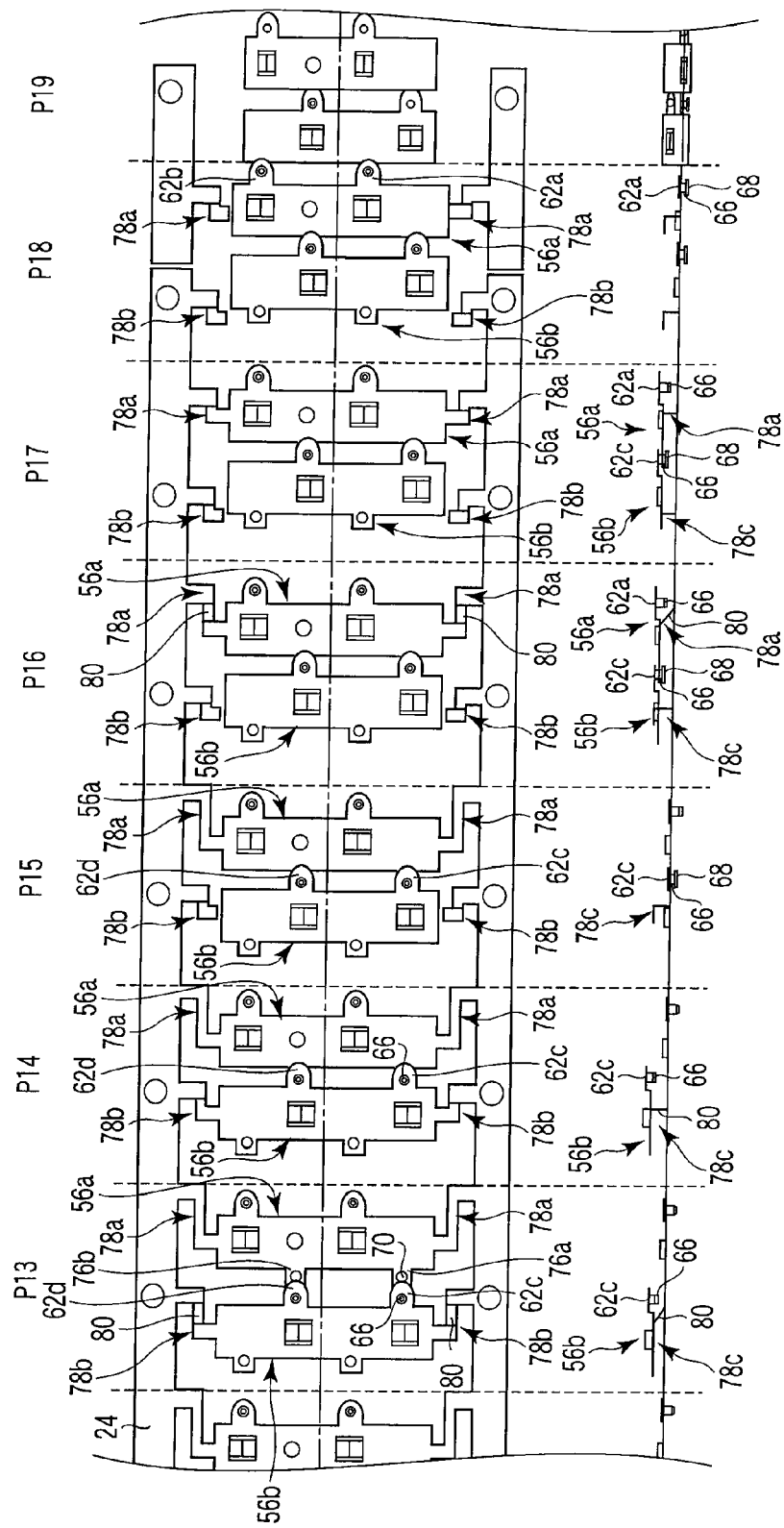
FIG. 4C is a third diagram for explaining the press processing of the plate material in the method of manufacturing the endoscopic insertion portion in the first embodiment of the present invention.
Figure 4D:
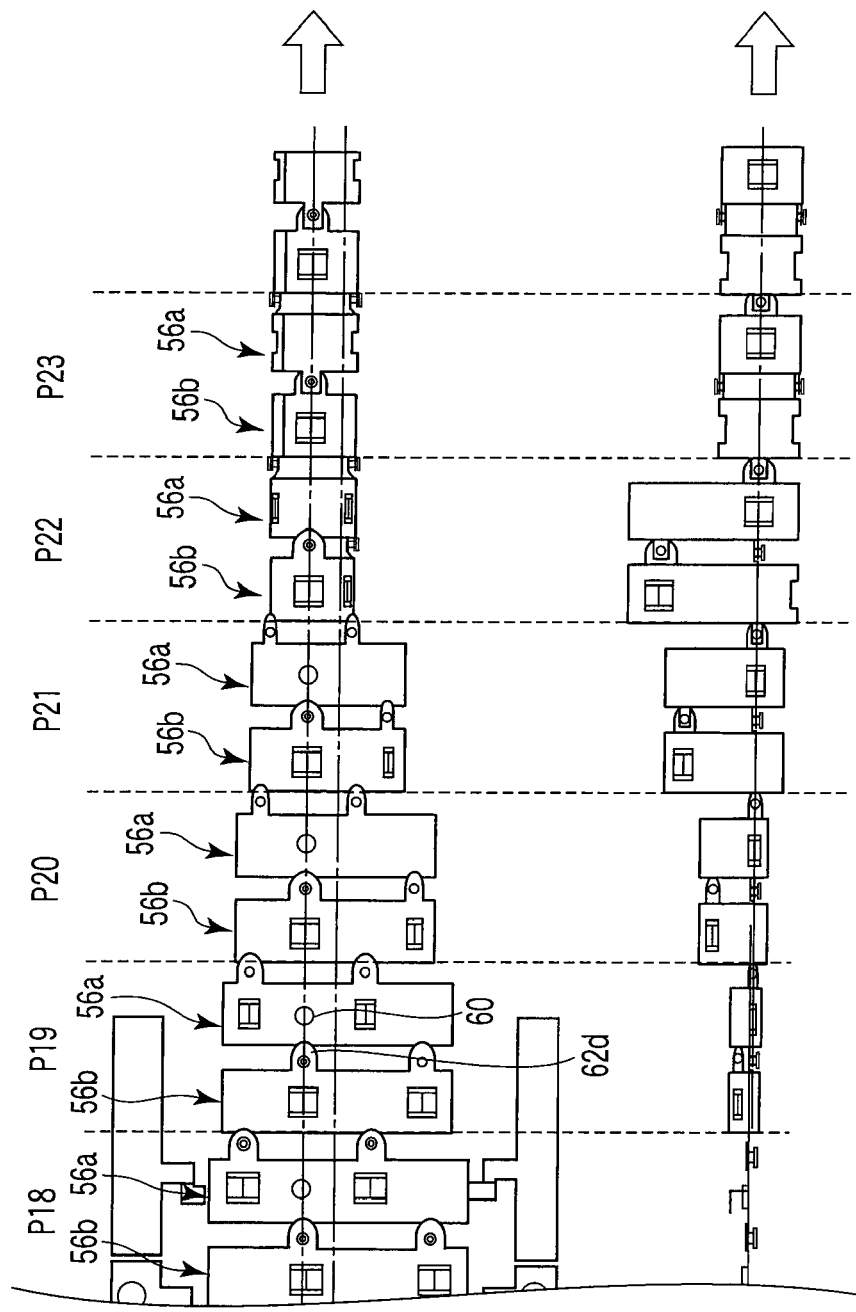
FIG. 4D is a fourth diagram for explaining the press processing of the plate material in the method of manufacturing the endoscopic insertion portion in the first embodiment of the present invention.

The outline of a method of manufacturing the bending portion will be described referring to FIG. 3. A plate material 24 is used to manufacture the bending portion, and as the plate material 24, use is, for example, a metal plate material such as a stainless steel plate material, a spring steel plate material or a nonferrous spring plate material including phosphor bronze and others; a resin plate material; or a composite plate material in which the layers containing the above materials as the main elements are stacked, or a composite plate material additionally containing a reinforcing material. This plate material 24 is wound and held around an uncoiler 40, and the plate material 24 guided out of the uncoiler 40 is corrected into a flat surface by a leveler 42. The plate material 24 guided out of the leveler 42 is guided into a progressive die 46 of a pressing machine by a feeder 44.

This progressive die 46 is formed of a punch holder 48 serving as an upper die and a die holder 49 serving as a lower die 49. First to twenty third punches 52a, . . . , 52w are provided side by side at regular intervals in a punch plate 50 of the punch holder 48, and first to twenty third dies 55a, . . . , 55w are provided side by side at regular intervals in a die plate 54 of the lower holder 49. The first to twenty third punches 52a, . . . , 52w and the first to twenty third dies 55a, . . . , 55w are opposite to each other such that first to twenty third processing positions P1, . . . , P23 are formed. The plate material 24 is intermittently fed as much as spaces between the processing positions P1, . . . , P23 by the feeder 44, and passed on to the first to twenty processing positions P1, . . . , P23 and thus continuously processed.

The method of manufacturing the bending tube will be described in detail for each separate step referring to FIG. 4A to FIG. 4E. In the present embodiment, the first and second bending part preparation portions 56a and 56b are simultaneously processed to form the adjacent first and second bending parts 26 coupled to each other at the processing positions P1, ..., P23.

Step 1 (First Processing Position P1)

A first pair of pilot holes 58 and a second pilot hole 60 are formed by blanking processing. By means of these pilot holes 58 and 60 the plate material 24 is positioned at the processing positions P1, ..., P23 in the following processing steps. The first pair of pilot holes 58 is formed at both ends in the width direction of the plate material 24 and used in various kinds of processing from Step 2 to Step 18. On the other hand, the second pilot hole 60 is formed off the center line by a certain distance in the width direction of the plate material 24, and used in various kinds of processing from Step 19 to Step 23.

At the same time, lancing portions 64 for the drawing processing of hinge protruding portion preparation portions 66 for forming the hinge protruding portions 30 are formed in a first pair of protruding portion tongue piece portion preparation portions 62a and 62b for forming the first pair of protruding portion tongue piece portions 28 of the first bending part 26 and in a second pair of protruding portion tongue piece portion preparation portions 62c and 62d for forming the second pair of protruding portion tongue piece portions 28 of the second bending part 26.

The first pair of protruding portion tongue piece portion preparation portions 62a and 62b is provided side by side in the width direction of the plate material 24, and the second pair of protruding portion tongue piece portion preparation portions 62c and 62d is provided side by side in the width direction of the plate material 24 in the rear of the first pair of protruding portion tongue piece portion preparation portions 62a and 62b. The protruding portion tongue piece portion preparation portion 62d which is one of the second pair of protruding portion tongue piece portion preparation portions 62c and 62d is disposed substantially in the middle of the first pair of protruding portion tongue piece portion preparation portions 62a and 62b with respect to the width direction of the plate material 24. Here, the length between the first pair of protruding portion tongue piece portion preparation portions 62a and 62b (the length between the second pair of protruding portion tongue piece portion preparation portions 62c and 62d) in the width direction of the plate material 24 corresponds to the length between the first pair of protruding portion tongue piece portions 28 (the length between the second pair of protruding portion tongue piece portions 28) in the circumferential direction of the bending part 26.

Step 2 (Second Processing Position P2)

In Step 2 to Step 8, the hinge protruding portion preparation portions 66 are formed in the protruding portion tongue piece portion preparation portions 62a, 62b, 62c and 62d.

In Step 2, hemispherical recesses 88 are formed by drawing processing which protrudes from a side serving as an inner peripheral surface of the bending part 26 to a side serving as an outer peripheral surface thereof (from the front side to rear side of the page bearing the drawing).

Step 3 to Step 5 (Third to Fifth Processing Positions P3, P4 and P5)

In Step 3 to Step 5, the hemispherical recesses 88 formed in Step 2 are sequentially deformed by drawing processing into cylindrical recesses 90 whose ends are blocked.

Step 6 (Sixth Processing Position P6)

In Step 6 and Step 7, diameter expanded portion preparation portions 68 for forming the diameter expanded portions 68a of the hinge protruding portions 30 are formed.

In Step 6, bores 92 are formed by punching processing substantially in the centers of end walls of the recesses 90 formed in Step 2 to Step 5.

Step 7 (Seventh Processing Position P7)

Peripheral edges of the bores 92 formed in Step 6 are extended by burring processing from the side serving as the inner peripheral surface of the bending part 26 to the side serving as the outer peripheral surface thereof (from the front side to rear side of the page bearing the drawing), and the substantially cylindrical diameter expanded portion preparation portions 68 become protruded manner in the end walls of the recesses 90 (see FIG. 4E).

Step 8 (Eighth Processing Position P8)

Hinge hole preparation portions 70 as receiving portion preparation portions for forming the hinge holes 34 of the first pair of receiving portion tongue piece portions 32 are formed by punching processing in the vicinity of the front end side of the second pair of protruding portion tongue piece portion preparation portions 62c and 62d in the longitudinal direction of the plate material 24. At the same time, hinge hole preparation portions 70 for forming the hinge holes 34 of the second pair of receiving portion tongue piece portions 32 are formed by punching processing in the vicinity of the front end side of the first pair of protruding portion tongue piece portion preparation portions 62a and 62b in Step 7 in the longitudinal direction of the plate material 24.

Step 9 (Ninth Processing Position P9)

In Step 9 and Step 10, there are formed a first pair of wire receiving portion preparation portions 72a and 72b for forming the first pair of wire receiving portions 36 of the first bending part 26, and a second pair of wire receiving portion preparation portions 72c and 72d for forming the second pair of wire receiving portions 36 of the second bending part 26.

In Step 9, there are formed first and second pairs of slit sets 75a, 75b, 75c and 75d respectively defining front end faces and rear end faces of the first and second pairs of wire receiving portions 36 in the rear of the first and second pairs of protruding portion tongue piece portion preparation portions 62a, 62b, 62c and 62d in the longitudinal direction of the plate material 24. The slit set 75a, 75b, 75c, 75d is formed by two slits extending in the width direction of the plate material 24 and provided side by side with each other. Here, the length of the slit in the width direction of the plate material 24 corresponds to the length of the wire receiving portion 36 in the circumferential direction of the bending part 26, and the distance between the slits in the slit set 75a, 75b, 75c, 75d corresponds to the length of the wire receiving portion 36 in the axial direction of the bending part 26.

Step 10 (Tenth Processing Position P10)

Parts between the slits in the first and second pairs of slit sets 75a, 75b, 75c and 75d are bent in V shape from the side serving as the outer peripheral surface of the bending part 26 to the side serving as the inner peripheral surface thereof (from the rear side to front side of the page bearing the drawing), thereby completing the first to fourth wire receiving portion preparation portions 72a, 72b, 72c and 72d.

It is to be noted that Step 9 and Step 10 may be carried out in one step by cutting-bending processing which simultaneously archives the slit formation and the bending processing.

Step 11 (Eleventh Processing Position P11)

In Step 11, the first and second bending part preparation portions 56a and 56b for forming the first and second bending parts 26 are formed by punching processing.

The first and second bending part preparation portions 56a and 56b have first and second long plate-shaped circumferential portion preparation portions 74a and 74b respectively forming the circumferential portions 27 of the bending parts 26 and extending in the width direction of the plate material 24. The first and second pairs of protruding portion tongue piece portion preparation portions 62a, 62b, 62c and 62d for respectively forming the first and second pairs of protruding portion tongue piece portions 28 extend in the longitudinal direction of the plate material 24 from the front end sides of the first and second circumferential portion preparation portions 74a and 74b. The hinge protruding portion preparation portions 66 described above have been formed in the first and second pairs of protruding portion tongue piece portion preparation portions 62a, 62b, 62c and 62d. On the other hand, first and second pairs of receiving portion tongue piece portion preparation portions 76a, 76b, 76c and 76d for forming the first and second pairs of receiving portion tongue piece portions 32 extend from the rear end sides of the first and second circumferential portion preparation portions 74a and 74b. The hinge hole preparation portions 70 described above have been formed in the first and second pairs of receiving portion tongue piece portion preparation portions 76a, 76b, 76c and 76d.

Furthermore, the first and second bending part preparation portions 56a and 56b are coupled to both edges of the plate material 24 by first and second pairs of support portions 78a and 78b. These support portions 78a and 78b extend from both edges of the plate material 24 inwardly in the width direction of the plate material 24, and then extend from the front end side to the rear end side in the longitudinal direction of the plate material 24, and again extend inwardly in the width direction of the plate material 24, thus being coupled to the ends of the first and second circumferential portion preparation portions 74a and 74b of the first and second bending part preparation portions 56a and 56b. Here, portions on both end sides of the support portions 78a and 78b are called connection portions, and intermediate portions thereof are called rise portions 80.

Step 12 (Twelfth Processing Position P12)

Step bending processing is carried out in connection portions between the circumferential portion preparation portions 74a and 74b and the protruding portion tongue piece portion preparation portions 62a, 62b, 62c and 62d, and the protruding portion tongue piece portion preparation portions 62a, 62b, 62c and 62d are arranged substantially parallel to the circumferential portion preparation portions 74a and 74b on the side serving as the inner peripheral surface of the bending part 26 (front side of the page bearing the drawing) of the circumferential portion preparation portions 74a and 74b.

Step 13 (Thirteenth Processing Position P13)

In Step 13 and Step 14, the rise portions 80 of the second pair of support portions 78b are raised from the side serving as the outer peripheral surface of the bending part 26 to the side serving as the inner peripheral surface thereof (from the rear side to front side of the page bearing the drawing) and to the front end side with respect to the plate material 24 by Z-shape bending processing in the second pair of support portions 78b supporting the second bending part preparation portion 56b. Then, the second bending part preparation portion 56b is moved from the side serving as the outer peripheral surface of the bending part 26 to the side serving as the inner peripheral surface thereof (from the rear side to front side of the page bearing the drawing) and to the front end side. As a result, the hinge protruding portion preparation portions 66 of the second pair of protruding portion tongue piece portion preparation portions 62c and 62d on the front end side of the second bending part protruding portion 56b are aligned with the hinge hole preparation portions 70 of the first pair of receiving portion tongue piece portion preparation portions 76a and 76b on the rear end side of the first bending part protruding portion 56a, respectively.

The former half of the necessary Z-shape bending processing is carried out in Step 13.

Step 14 (Fourteenth Processing Position P14)

The latter half of the necessary Z-shape bending processing is carried out.

Step 15 (Fifteenth Processing Position P15)

The second bending part preparation portion 56b is struck down from the side serving as the inner peripheral surface of the bending part 26 to the side serving as the outer peripheral surface thereof (from the front side to rear side of the page bearing the drawing) by dropping processing, thereby separating the second bending part preparation portion 56b from the plate material 24. As a result, the hinge protruding portion preparation portions 66 of the second bending part preparation portion 56b are inserted rotatably in the hinge hole preparation portions 70 of the first bending part preparation portion 56a. Moreover, the second bending part preparation portion 56b is cut off from the second pair of support portions 78b.

At the same time, the substantially cylindrical diameter expanded portion preparation portions 68 at the extending ends of the hinge protruding portion preparation portions 66 are pushed open through enlarging-opening processing by pushing the dies therein from the side serving as the outer peripheral surface of the bending part 26 to the side serving as the inner peripheral surface thereof (from the rear side to front side of the page bearing the drawing), thereby forming the diameter expanded portion 68a.

The first and second bending part preparation portions 56a and 56b after Step 15 has been finished are shown in FIG. 5.

Step 16 (Sixteenth Processing Position P16)

In Step 16 and Step 17, the rise portions 80 of the first pair of support portions 78a are raised from the side serving as the outer peripheral surface of the bending part 26 to the side serving as the inner peripheral surface thereof (from the rear side to front side of the page bearing the drawing) and to the front end side with respect to the plate material 24 by Z-shape bending processing in the first pair of support portions 78a supporting the first bending part preparation portion 56a. Then, both the first and second bending part preparation portions 56a and 56b are moved from the side serving as the outer peripheral surface of the bending part 26 to the side serving as the inner peripheral surface thereof (from the rear side to front side of the page bearing the drawing) and to the front end side.

The former half of the necessary Z-shape bending processing is carried out in Step 16.

Step 17 (Seventeenth Processing Position P17)

The latter half of the necessary Z-shape bending processing is carried out.

Step 18 (Eighteenth Processing Position P18)

With respect to the vertical direction of the plate material 24, the hinge protruding portion preparation portions 66 of the first pair of protruding portion tongue piece portion preparation portions 62a and 62b on the front end side of the first bending part preparation portion 56a are aligned with the hinge hole preparation portions 70 of the second pair of receiving portion tongue piece portion preparation portions 76c and 76d on the rear end side of the second bending part preparation portion 56b disposed on the front end side, respectively. Subsequently, as in the fifteenth step, the first bending part preparation portion 56a is struck down by dropping processing to separate the first bending part preparation portion 56a from the plate material 24, and the diameter expanded portions 68a are formed by enlarging-opening processing, so that the first bending part preparation portion 56a is connected to the second bending part preparation portion 56b disposed on the front end side.

Step 19 to Step 22 (Nineteenth to Twenty Second Processing Positions P19, P20, P21 and P22)

In Step 19 to Step 22, the first and second bending part preparation portions 56a and 56b including the first and second protruding portion tongue piece portion preparation portions 62a, . . . , 62d are gradually bent in a U shape up to a final R (curvature) from the side serving as the outer peripheral surface of the bending part 26 to the side serving as the inner peripheral surface thereof (from the rear side to front side of the page bearing the drawing).

It is to be noted that the second pilot hole 60 serving as a reference for the positioning of the plate material 24 is disposed on a line passing the center of the pair of protruding portion tongue piece portion preparation portions 62a and 62b on the first bending part preparation portion 56a, and the U-shape bending processing of the plate material 24 is carried out using the above-mentioned line as the base line.

Step 23 (Twenty Third Processing Position P23)

The first and second bending part preparation portions 56a and 56b which have been bent in a U shape are further subjected to O-shape bending processing, thereby forming the first and second cylindrical bending parts 26. At this point, both end faces of the first and second bending part preparation portions 56a and 56b face and abut against each other.

Step 24

After Step 1 to Step 23, the bending tube is discharged from the pressing machine. In this bending tube, a plurality of substantially cylindrical bending parts 26 are coupled to each other and arranged side by side and the abutting portions in the bending parts 26 are disposed substantially at the same position with respect to the circumferential direction of the bending parts 26. Then, two places in the abutting portions of the bending part 26 are joined in the spot shape by the laser welding and others. Subsequently, in order to obtain a bending tube having a desired length corresponding to the length of the bending portion, the protruding portion tongue piece portions 28 and the receiving portion tongue piece portions 32 at both ends of a certain number of coupled bending parts 26 are cut and removed to enable both ends to be fit and fixed to the rear end portion of the distal end forming portion 14 and the front end portion of the insertion tube portion 18. Alternatively, before Step 10, the protruding portion tongue piece portions 62a and 62b may be punched off every number of protruding portion tongue piece portions 62a and 62b corresponding to a desired number of coupling of bending parts so that the hinge protruding portions 30 are not formed, thereby automatically obtaining the bending tube having the desired length corresponding to the length of the bending portion.

Therefore, the present embodiment provides the following advantages.

In the bending tube of the present embodiment, the bending parts 26, the hinge protruding portions 30 and the hinge holes 34 are formed from the single plate material 24 by press processing. That is, in the method of manufacturing the bending tube in the present embodiment, the hinge protruding portion preparation portions 66 and the hinge hole preparation portions 70 are formed in the plate material 24 by press processing, and the first or second bending part preparation portion 56a or 56b having the hinge protruding portion preparation portions 66 or the hinge hole preparation portions 70 is formed by punching processing. Then, one of the first and second bending part preparation portions 56a and 56b is moved by Z-shape bending processing to align the hinge protruding portion preparation portions 66 with the hinge hole preparation portions 70 in a direction vertical to the plate material 24, and one of the first and second bending part preparation portions 56a and 56b is subjected to the dropping processing, thereby inserting the hinge protruding portion preparation portions 66 in the hinge hole preparation portions 70 rotatably. In addition, the bending part preparation portions 56a and 56b are bent in a U shape and further bent in an O shape, such that the bending tube is manufactured. Thus, the bending tube can be formed only by press processing, so that the efficiency of manufacturing the endoscopic insertion portion 12 is improved.

Furthermore, in all the steps described above, the first and second bending part preparation portions 56a and 56b are simultaneously processed at the processing positions for carrying out the respective steps, and the plate material 24 is passed on to the processing positions for carrying out the respective steps in the order described above and is processed continuously. Thus, the efficiency of manufacturing the endoscopic insertion portion 12 is further improved.

In addition, the bending parts 26 in the present embodiment are in a continuous cylindrical shape in which both ends of the first and second bending part preparation portions 56a and 56b abutting against each other due to the O-shape bending processing are joined, so that the resistance of the bending parts 26 to external force is improved.

Still further, in the manufacturing process of the bending tube of the endoscopic insertion portion 12 in the present embodiment, the wire receiving portion preparation portions 72a, 72b, 72c and 72d are formed by the slit processing and bending processing of the plate material 24. Thus, the wire receiving portions 36 can be continuously formed at one time together with the bending parts 26 by the same pressing machine, so that the efficiency of manufacturing the endoscopic insertion portion 12 is drastically improved.

Figure 6:
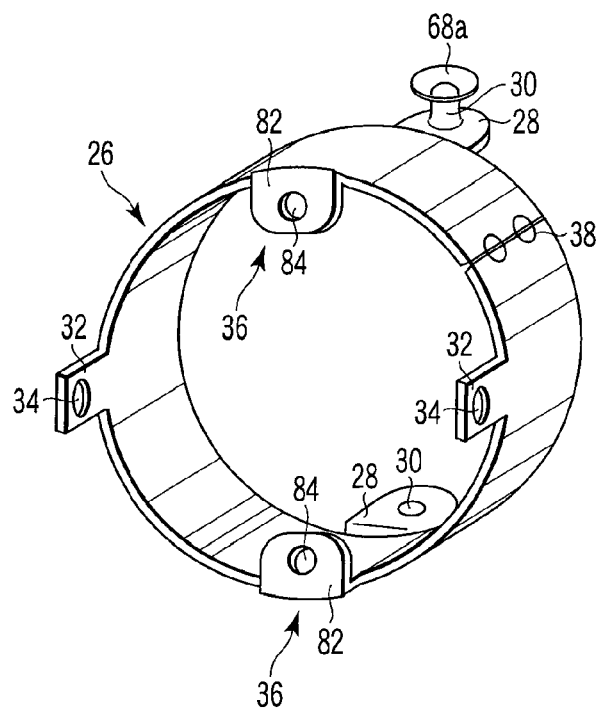
FIG. 6 is a perspective view showing a bending part of a bending tube of an endoscope in a modification of a second embodiment of the present invention.
Figure 7:
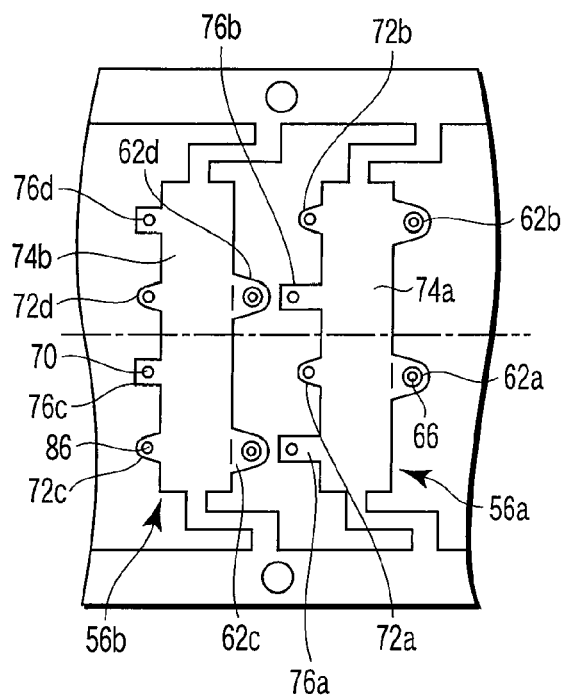
FIG. 7 is a diagram for explaining the press processing of a plate material in a method of manufacturing an endoscopic insertion portion in the modification of the second embodiment of the present invention.

FIGS. 6 and 7 show a first modification of the first embodiment of the present invention. The same reference numerals are assigned to the components having functions similar to those in the first embodiment, and these components are not described.

As shown in FIG. 6, in the bending part 26 of the bending tube in the present modification, the pair of wire receiving portions 36 is disposed on one end face in which the pair of receiving portion tongue piece portions 32 is disposed, at such positions that the pair of receiving portion tongue piece portions 32 is rotationally moved 90° when viewed in the direction of the central axis of the bending part 26. That is, the pair of wire receiving portions 36 is provided side by side with the protruding portion tongue piece portions 28 in the direction of the central axis of the bending part 26. The pair of wire receiving portions 36 is in a form in which wire insertion holes 84 are formed to penetrate in the direction of the central axis of the bending part 26 in wire tongue piece portions 82 protruding diametrically inwardly from the bending part 26.

A method of manufacturing the bending tube of the endoscopic insertion portion 12 in the present modification will be described referring to FIG. 7.

Step 1 to Step 8 are similar to Step 1 to Step 8 in the first embodiment before the wire receiving portion preparation portions 72a, 72b, 72c and 72d are formed. In Step 9, wire insertion hole preparation portions 86 for forming the wire insertion holes 84 of the wire receiving portions 36 are formed by punching processing. In Step 10, the first and second bending part preparation portions 56a and 56b for forming the first and second bending parts 26 are formed by punching processing. As shown in FIG. 7, the first and second pairs of wire receiving portion preparation portions 72a, 72b, 72c and 72d for forming the first and second pairs of wire receiving portions 36 of the first and second bending parts 26 extend from the rear end sides of the first and second circumferential portion preparation portions 74a and 74b of the first and second bending part preparation portions 56a and 56b, and the wire insertion hole preparation portions 86 described above have been formed in the wire receiving portion preparation portions 72a, 72b, 72c and 72d. The first and second pairs of wire receiving portion preparation portions 72a, 72b, 72c and 72d are provided side by side with the first and second pairs of protruding portion tongue piece portion preparation portions 62a, 62b, 62c and 62d in the longitudinal direction of the plate material 24. Then, in Step 11, the first and second pairs of wire receiving portion preparation portions 72a, . . . , 72d are bent from the side serving as the outer peripheral surface of the bending part 26 to the side serving as the inner peripheral surface thereof (from the rear side to front side of the page bearing the drawing). The subsequent steps are similar to Step 12 to Step 23 in the first embodiment starting with the Z-shape bending processing.

A second embodiment of the present invention will hereinafter be described.

In the present embodiment, after the bending tube has been discharged from the pressing machine, the manufacture of the bending tube is finished in a situation where both end faces of the bending part preparation portions 56a and 56b are pressed and in abutment against each other without joining the abutting portions of the bending part 26. Thus, the manufacture of the bending tube can be completed only by press processing, and the manufacturing process of the bending tube is simplified.

A third embodiment of the present invention will hereinafter be described.

In the present embodiment, an insertion tube forming the insertion tube portion 18 is configured in the same manner as the bending portion 16 in the first embodiment, and the bending tube and the insertion tube are formed from a single plate material by press processing. However, the wire receiving portions 36 are not used in the insertion tube. In the present embodiment, the bending tube and the insertion tube can be continuously manufactured at one time only by press processing, so that the manufacturing process of the endoscopic insertion portion 12 is simplified.

It is to be noted that the bending tube is formed by progressive press processing in the embodiment described above, but the bending tube can also formed by press processing other than the progressive press processing. For example, for all the bending parts 26 forming the bending tube, Step 1 in the first embodiment may be carried out with a first die, and Step 2 may be carried out with a second die in a collective manner. Moreover, the steps before the U-shape bending processing in the first embodiment may be carried out by the progressive press processing, and the U-shape bending processing and the O-shape bending processing may be collectively carried out for all the bending parts 26 forming the bending tube.

The hinge holes in the shape of through holes are used as receiving portions in the embodiment described above, but concave hinge recesses into which the hinge protruding portions are inserted rotatably may be used.

A fourth embodiment of the present invention will hereinafter be described with reference to FIG. 8A to FIG. 9C.

Referring to FIG. 1, FIG. 8A and FIG. 8B, a plurality of thin and cylindrical bending parts 26 of one kind except for the bending parts at the front and rear ends respectively coupled to the distal end forming portion 14 and the insertion tube portion 18 are coaxially coupled to each other and arranged side by side in a bending tube 94 forming the framework of the bending portion 16.

On one end face of the circumferential portion 27 of the bending part 26, the pair of receiving portion tongue piece portions 32 is provided to protrude in the direction of the central axis of the bending tube 94 at positions symmetrical with respect to the central axis. Steps oriented inward in the diametrical direction of the bending tube 94 are formed to correspond to the thickness of the plate of the bending part 26 in connection portions between the circumferential portion 27 of the bending part 26 and the receiving portion tongue piece portions 32, and the receiving portion tongue piece portions 32 are disposed substantially parallel to the circumferential portion 27 inside the circumferential portion 27 in the diametrical direction and serve as a minor diameter circumferential portion. Then, through holes 98 roundly shaped in section are formed in the receiving portion tongue piece portions 32 to penetrate in the diametrical direction of the bending tube 94.

On the other hand, the pair of protruding portion tongue piece portions 28 is provided on the other end face of the bending part 26 to protrude in the direction of the central axis of the bending tube 94 at such positions that the pair of receiving portion tongue piece portions 32 is rotationally moved about 90° when viewed in the direction of the central axis of the bending tube 94. The protruding portion tongue piece portions 28 are disposed substantially parallel to the circumferential portion 27 of the bending part 26, and have about the same diameter as that of the circumferential portion 27. Further, protruding portions 100 are protruded from the protruding portion tongue piece portions 28, and these protruding portions 100 are formed by bending parts of the protruding portion tongue piece portions 28 by press processing and have convex zonal shapes oriented inward in the diametrical direction of the bending tube 94. That is, hole portions roundly shaped in section are formed in the protruding portion tongue piece portions 28 to penetrate in the diametrical direction of the bending tube 94, and the protruding portions 100 have semicircular zonal shapes which connect both end positions in the circumferential direction of the bending tube 94 in the peripheral edges of the hole portions and which are diametrically inwardly convex when viewed in the direction of the central axis of the bending tube 94.

In the case where a plurality of bending parts 26 are provided side by side with each other, the adjacent two bending parts 26 are disposed so that they are displaced by about 90° from each other when viewed in she direction of the central axis of the bending tube 94. Further, the protruding portion tongue piece portions 28 and the receiving portion tongue piece portions 32 which are respectively protruded from the end faces of the adjacent two bending parts 26 are made to overlap each other, and the protruding portions 100 of the protruding portion tongue piece portions 28 are inserted rotatably in the through holes 98 as the receiving portions of the receiving portion tongue piece portions 32. A pair of protruding portions 100 is rotated in the pair of through holes 98 between the adjacent two bending parts 26, such that these two bending parts 26 swing with respect to each other. Moreover, the direction in which the bending part 26 on the front end side of a certain bending part 26 swings with respect to the certain bending part 26 is substantially perpendicular to the direction in which the bending part 26 on the rear end side of the certain bending part 26 swings with respect to the certain bending part 26, and the combination of such swings of the bending parts 26 enables the bending tube 94 to bend in any direction.

Here, wire insertion holes 102 through which the operation wires for the bending operation of the bending portion 16 are inserted are formed in the protruding portions 100. That is, as described above, the protruding portions 100 have semicircular zonal shapes which connect both end positions in the circumferential direction of the bending tube 94 in the peripheral edges of the hole portions of the protruding portion tongue piece portions 28 and which are diametrically inwardly convex when viewed in the direction of the central axis of the bending tube 94. Thus, the insertion holes 102 are formed by the protruding portions 100 in the direction of the central axis of the bending tube 94. Here, the insertion holes 102 formed by the pairs of protruding portions 100 of the respective bending part 26 are arranged so that they are formed in alternate positions in the axial direction of the bending tube 94 sequentially with respect to the observation field of the endoscope 10, for example, at vertical positions, at horizontal positions, at vertical positions, at horizontal positions, and so on. The operation wires for vertical and horizontal bending operations are inserted through the insertion holes 102 at the vertical and horizontal positions, so that the bending portion 16 can be operated to bend in vertical and horizontal directions.

In addition, as described later in detail, the bending part 26 is formed by deforming a long plate-shaped bending part preparation portion 56a, 56b (see FIG. 9A to FIG. 9C) into a cylindrical shape, and causing end faces at both ends thereof to abut against each other, and then joining the abutting portions by laser welding and others. The junction 38 extending over the entire length of the bending part 26 in the axial direction of the bending portion 16 is formed in the bending part 26. This junction 38 may be formed by welding the abutting portions by laser spot welding at one point or two or more points.

Next, a method of manufacturing the endoscopic insertion portion 12 in the present embodiment will be described.

Figure 9A:
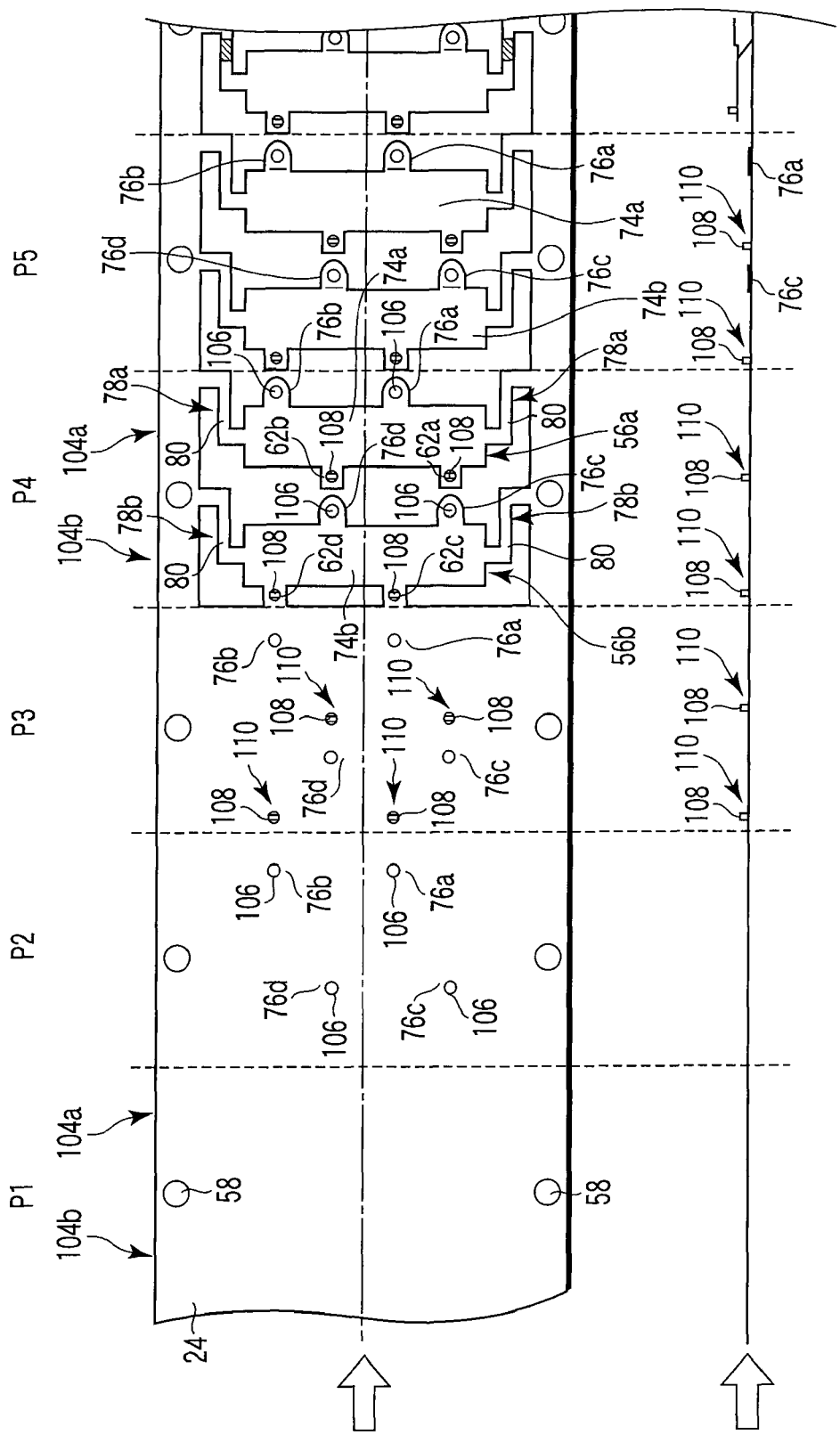
FIG. 9A is a first diagram for explaining the press processing of a plate material in a method of manufacturing the endoscopic insertion portion in the fourth embodiment of the present invention.
Figure 9B:
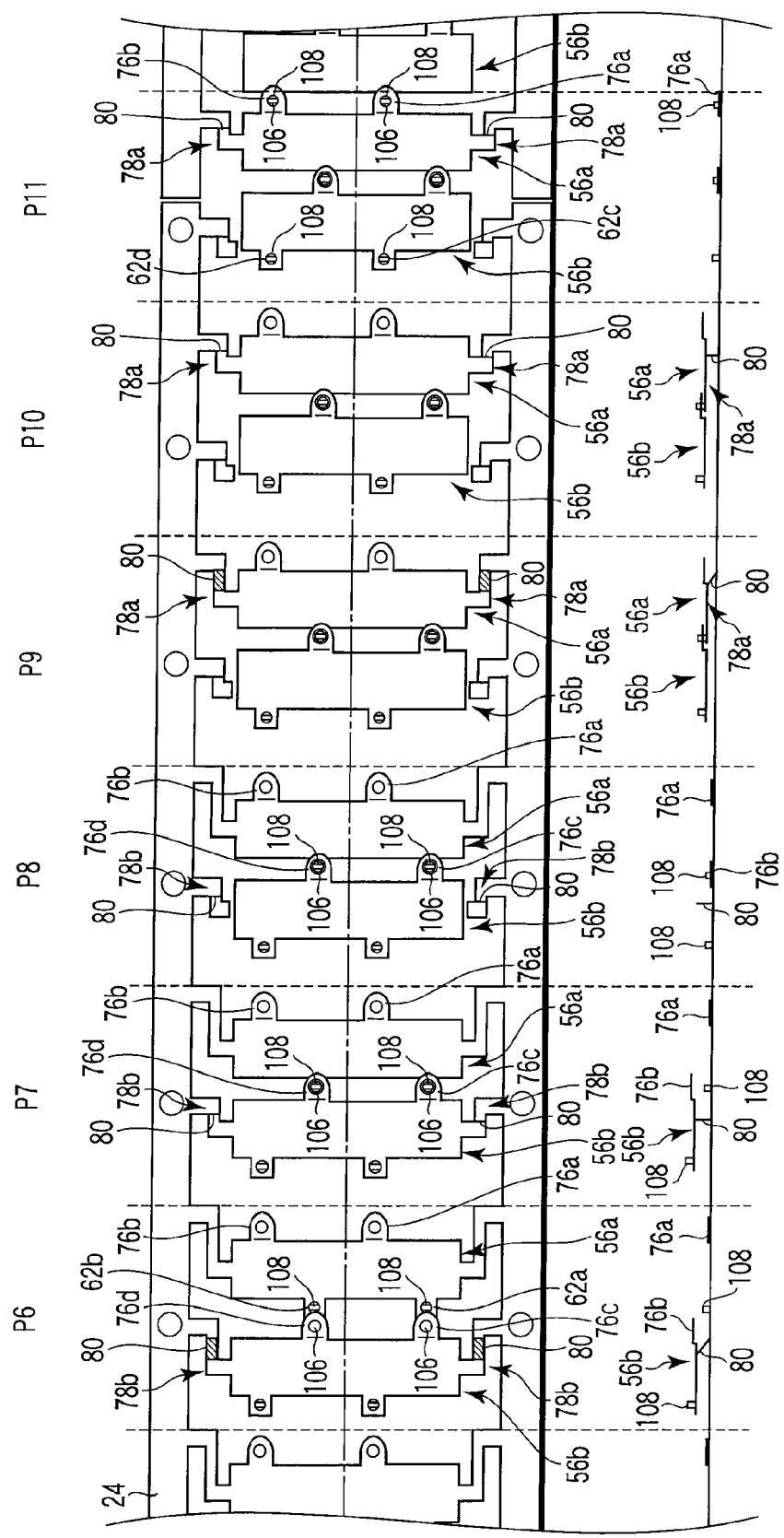
FIG. 9B is a second diagram for explaining the press processing of the plate material in the method of manufacturing the endoscopic insertion portion in the fourth embodiment of the present invention.
Figure 9C:
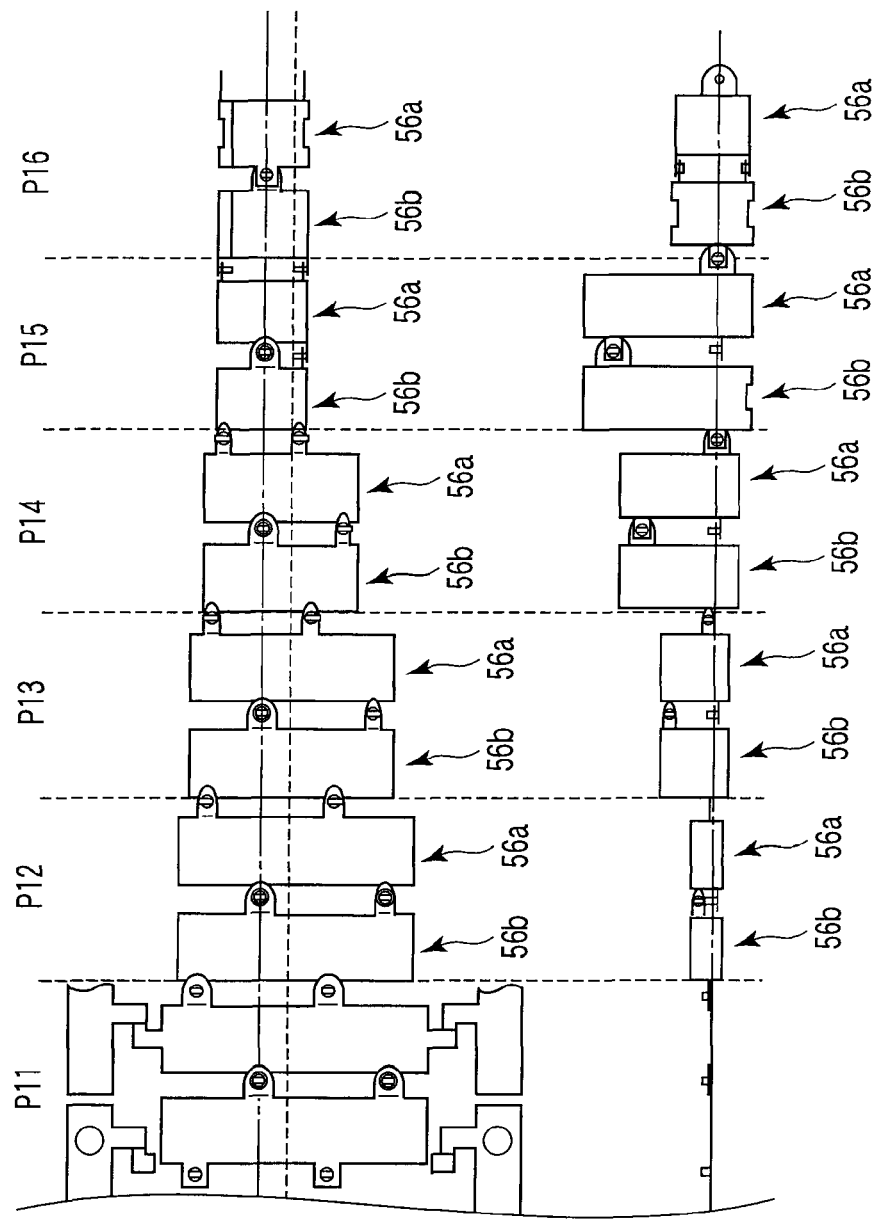
FIG. 9C is a third diagram for explaining the press processing of the plate material in the method of manufacturing the endoscopic insertion portion in the fourth embodiment of the present invention.

A method of manufacturing the bending tube 94 will be described in detail for each separate step with reference to FIG. 9A to FIG. 9C. In the present embodiment, the first and second bending part preparation portions 56a and 56b are simultaneously processed, and processed in pairs, in order to form the adjacent first and second bending parts 26 and couple them to each other at the processing positions P1, ..., P16.

Step 1 (First Processing Position P1)

The pilot holes 58 are formed at both ends in the width direction of the plate material 24. By means of these pilot holes 58, the plate material 24 is positioned at the processing positions in the following processing steps.

Step 2 (Second Processing Position P2)

Through hole preparation portions 106 serving as preparation holes for forming the through holes 98 of the receiving portion tongue piece portions 32 are formed by punching processing at positions corresponding to the first pair of receiving portion tongue piece portion preparation portions 76a and 76b for forming the first pair of receiving portion tongue piece portions 32 of the first bending part 26 and the second pair of receiving portion tongue piece portion preparation portions 76c and 76d for forming the second pair of receiving portion tongue piece portions 32 of the second bending part 26.

The first pair of receiving portion tongue piece portion preparation portions 76a and 76b is provided side by side in the width direction of the plate material 24, and the second pair of receiving portion tongue piece portion preparation portions 76c and 76d is provided side by side in the width direction of the plate material 24 in the rear of the first pair of receiving portion tongue piece portion preparation portions 76a and 76b. The receiving portion tongue piece portion preparation portion 76d which is one of the second pair of receiving portion tongue piece portion preparation portions 76c and 76d is disposed at a position substantially in the middle of the first pair of receiving portion tongue piece portion preparation portions 76a and 76b with respect to the width direction of the plate material 24. Here, the length between the first pair of receiving portion tongue piece portion preparation portions 76a and 76b (the length between the second pair of receiving portion tongue piece portion preparation portions 76c and 76d) in the width direction of the plate material 24 corresponds to the length between the first pair of receiving portion tongue piece portions 32 (the length between the second pair of receiving portion tongue piece portions 32) in the circumferential direction of the bending part 26.

Step 3 (Third Processing Position P3)

Protruding portion preparation portions 108 for forming the protruding portions 100 of the first pair of protruding portion tongue piece portions 28 are formed by press processing in the vicinity of the front end side of the second pair of receiving portion tongue piece portion preparation portions 76c and 76d in the longitudinal direction of the plate material 24. At the same time, protruding portion preparation portions 108 for forming the protruding portions 100 of the second pair of protruding portion tongue piece portions 28 are formed by press processing in the vicinity of the front end side of the first pair of receiving portion tongue piece portion preparation portions 76a and 76b in Step 2.

That is, in the protruding portion preparation portion 108, two semicircular holes are combined and the zonal portion which crosses the round hole portion to extend in the diametrical direction of this hole portion and in the width direction of the plate material 24 are formed by press processing. Then, this zonal portion is deformed by drawing processing of press processing so that it forms a semicircular shape which is convex from the side serving as the outer peripheral surface of the bending part 26 to the side serving as the inner peripheral surface thereof (from the rear side to front side of the page bearing the drawing) when viewed in the longitudinal direction of the plate material 24.

Here, in the protruding portion preparation portion 108, an opening is formed between the surface where the hole portion is formed and the zonal portion forming the convex semicircular shape when viewed in the longitudinal direction of the plate material 24, and this opening serves as an insertion hole preparation portion 110 for forming the wire insertion hole 102.

Step 4 (Fourth Processing Position P4)

In Step 4, the first and second bending part preparation portions 56a and 56b for forming the first and second bending parts 26 are formed by punching processing in a first plate-shaped portion 104a and a second plate-shaped portion 104b.

The first and second bending part preparation portions 56a and 56b have the first and second long plate-shaped circumferential portion preparation portions 74a and 74b forming the circumferential portions 27 of the bending parts 26 and extending in the width direction of the plate material 24. The first and second pairs of receiving portion tongue piece portion preparation portions 76a, 76b, 76c and 76d described above extend from the front end sides of the first and second circumferential portion preparation portions 74a and 74b. The through hole preparation portions 106 described above have been formed in the first and second pairs of receiving portion tongue piece portion preparation portions 76a, 76b, 76c and 76d. On the other hand, the first and second pairs of protruding portion tongue piece portion preparation portions 62a, 62b, 62c and 62d for forming the first and second pairs of protruding portion tongue piece portions 28 extend in the longitudinal direction of the plate material 24 from the rear end sides of the first and second circumferential portion preparation portions 74a and 74b. The above-mentioned protruding portion preparation portions 108 have been formed in the first and second pairs of protruding portion tongue piece portion preparation portions 62a, 62b, 62c and 62d.

Furthermore, both ends of the first and second bending part preparation portions 56a and 56b and both edges of the plate material 24 are coupled together by the first and second pairs of support portions 78a and 78b. These support portions 78a and 78b extend from both edges of the plate material 24 inwardly in the width direction of the plate material 24, and then extend from the front end side to the rear end side in the longitudinal direction of the plate material 24, and again extend inwardly in the width direction of the plate material 24, thus being coupled to the ends of the first and second circumferential portion preparation portions 74a and 74b of the first and second bending part preparation portions 56a and 56b. Here, portions on both end sides of the support portions 78a and 78b are called connection portions, and intermediate portions thereof are called rise portions 80.

Step 5 (Fifth Processing Position P5)

Step bending processing is carried out in connection portions between the circumferential portion preparation portions 74a and 74b and the receiving portion tongue piece portion preparation portions 76a, 76b, 76c and 76d, so that the receiving portion tongue piece portion preparation portions 76a, 76b, 76c and 76d protrude as much as the thickness of the bending part 26 to the side serving as the inner peripheral surface of the bending part 26 (the front side of the page bearing the drawing) from the circumferential portion preparation portions 74a and 74b, and the receiving portion tongue piece portion preparation portions 76a, 76b, 76c and 76d are arranged substantially parallel to the circumferential portion preparation portions 74a and 74b.

Step 6 (Sixth Processing Position P6)

In Step 6 and Step 7, the rise portions 80 of the second pair of support portions 78b supporting the second bending part preparation portion 56b are raised from the side serving as the outer peripheral surface of the bending part 26 to the side serving as the inner peripheral surface thereof (from the rear side to front side of the page bearing the drawing) and to the front end side with respect to the plate material 24 by Z-shape bending processing in the second pair of support portions 78b. Then, the second bending part preparation portion 56b is moved from the side serving as the outer peripheral surface of the bending part 26 to the side serving as the inner peripheral surface thereof (from the rear side to front side of the page bearing the drawing) and to the front end side. As a result, in the vertical direction of the plate material 24, the through hole preparation portions 106 of the second pair of receiving portion tongue piece portion preparation portions 76c and 76d on the front end side of the second bending part 26 are aligned with the protruding portion preparation portions 108 of the first pair of protruding portion tongue piece portion preparation portions 62a and 62b on the rear end side of the first bending part 26, respectively.

The former half of the necessary Z-shape bending processing is carried out in Step 6.

Step 7 (Seventh Processing Position P7)

The latter half of the necessary Z-shape bending processing is carried out.

Step 8 (Eighth Processing Position P8)

The second bending part preparation portion 56b is struck down from the side serving as the inner peripheral surface of the bending part 26 to the side serving as the outer peripheral surface thereof (from the front side to rear side of the page bearing the drawing) by dropping processing, thereby separating the second bending part preparation portion 56b from the plate material 24. As a result, the protruding portion preparation portions 108 of the first bending part preparation portion 56a are inserted rotatably in the through hole preparation portions 106 of the second bending part preparation portion 56b, and the second bending part preparation portion 56b is connected to the first bending part preparation portion 56a. Moreover, the second bending part preparation portion 56b is cut off from the second pair of support portions 78b.

Step 9 (Ninth Processing Position P9)

In Step 9 and Step 10, the rise portions 80 of the first pair of support portions 78a supporting the first bending part preparation portion 56a are raised from the side serving as the outer peripheral surface of the bending part 26 to the side serving as the inner peripheral surface thereof (from the rear side to front side of the page bearing the drawing) and to the front end side with respect to the plate material 24 by Z-shape bending processing in the first pair of support portions 78a. Then, both the first and second bending part preparation portions 56a and 56b are moved from the side serving as the outer peripheral surface of the bending part 26 to the side serving as the inner peripheral surface thereof (from the rear side to front side of the page bearing the drawing) and to the front end side.

The former half of the necessary Z-shape bending processing is carried out in Step 9.

Step 10 (Tenth Processing Position P10)

The latter half of the necessary Z-shape bending processing is carried out.

Step 11 (Eleventh Processing Position P11)

The through hole preparation portions 106 of the first pair of receiving portion tongue piece portion preparation portions 76a and 76b on the front end side of the first bending part preparation portion 56a are aligned with the protruding portion preparation portions 108 of the second pair of protruding portion tongue piece portion preparation portions 62c and 62d on the rear end side of the second bending part preparation portion 56b disposed on the front end side, respectively. Subsequently, as in the eighth step, the first bending part preparation portion 56a is separated from the plate material 24 by dropping processing, and the first bending part preparation portion 56a is connected to the second bending part preparation portion 56b disposed on the front end side.

Step 12 to Step 15 (Twelfth to Fifteenth Processing Positions P12, P13, P14 and P15)

In Step 12 to Step 15, the circumferential portion preparation portions 74a and 74b, the receiving portion tongue piece portion preparation portions 76a, 76b, 76c and 76d, and the protruding portion tongue piece portion preparation portions 62a, 62b, 62c and 62d of the first and second bending part preparation portions 56a and 56b are gradually bent in a U shape up to a final R (curvature) from the side serving as the outer peripheral surface of the bending part 26 to the side serving as the inner peripheral surface thereof (from the rear side to front side of the page bearing the drawing).

Step 16 (Sixteen Processing Position P16)

The circumferential portion preparation portions 74a and 74b, the receiving portion tongue piece portion preparation portions 76a, 76b, 76c and 76d, and the protruding portion tongue piece portion preparation portions 62a, 62b, 62c and 62d of the first and second bending part preparation portions 56a and 56b which have been bent in a U shape are further subjected to O-shape bending processing, thereby forming the first and second cylindrical bending parts 26. At this point, both end faces of the first and second bending part preparation portions 56a and 56b face and abut against each other.

Step 17

After Step 1 to Step 16, the bending tube 94 is discharged from a pressing machine 47. Then, the abutting portions of the bending part 26 are joined by forming the junction 38 by means of the laser welding and others.

Therefore, the present embodiment provides the following advantages.

The protruding portions 100 of the bending tube 94 in the present embodiment have the insertion holes 102 which are integrally provided in the bending part 26 by press processing and through which the operation wires are inserted. Specifically, the protruding portions 100 of the bending tube 94 are convex zonal portions which are provided integrally with the protruding portion tongue piece portions 28 by pressing parts of the protruding portion tongue piece portions 28 of the bending part 26 diametrically inwardly from the protruding portion tongue piece portions 28, and the insertion holes 102 through which the operation wires are inserted are formed by spaces formed between the convex zonal portions and the protruding portion tongue piece portions 28. Such a bending tube 94 can be formed as follows: the protruding portion preparation portions 108 are formed in the first plate-shaped portion 104a by press processing, and the insertion hole preparation portions 110 are formed in the protruding portion preparation portions 108 by press processing, and then the first bending part preparation portion 56a is formed in the first plate-shaped portion 104a by punching processing. On the other hand, the through hole preparation portions 106 are formed in the second plate-shaped portion 104b by press processing, and the second bending part preparation portion 56b is formed by punching processing. Then, the first and second bending part preparation portions 56a and 56b are relatively moved to align the protruding portion preparation portions 108 with the through hole preparation portions 106, and the protruding portion preparation portions 108 are inserted rotatably in the through hole preparation portions 106 to connect the first and second bending part preparation portions 56a and 56b to each other. In addition, the bending part preparation portions 56a and 56b are bent in a U shape, and further bent in an O shape. Thus, in the present embodiment, the number of steps for processing the bending tube 94 is reduced, so that the cost of the bending tube 94 is reduced.

Furthermore, the bending tube 94 in the present embodiment is formed from bending parts 26 of one kind, and a certain bending part 26 has the protruding portions 100 for the through holes 98 of the bending part 26 provided side by side on one side of the certain bending part 26, and the through holes 98 for the protruding portions 100 of the bending part 26 provided side by side on the other side thereof. Such a bending tube 94 can be formed as follows: when the protruding portion preparation portions 108 are aligned with the through hole preparation portions 106, the bending part preparation portion 56b which is one of the first and second bending part preparation portions 56a and 56b is moved by the Z-shape bending processing, such that the protruding portion preparation portions 108 are aligned with the through hole preparation portions 106 in the direction vertical to the plate material 24. Further, when the first and second bending part preparation portions 56a and 56b are connected to each other, the bending part preparation portion 56b which is one of the first and second bending part preparation portions 56a and 56b is dropped so that the protruding portion preparation portions 108 are inserted rotatably in the through hole preparation portions 106. Thus, the alignment of the protruding portion preparation portions 108 with the through hole preparation portions 106 and the connection of the first and second bending part preparation portions 56a and 56b can be achieved with a reduced number of processing steps.

Still further, in all the steps described above, in order to simultaneously process the first and second bending part preparation portions 56a and 56b at the processing positions for carrying out the respective steps and handle them in pairs, the plate material 24 is passed on to the processing positions for carrying out the respective steps in the order described above and is continuously processed. Thus, the efficiency of manufacturing the bending tube 94 is drastically improved.

A first modification of the fourth embodiment will hereinafter be described.

The protruding portions 100 of the protruding portion tongue piece portions 28 of the bending part 26 in the present modification have a substantially cylindrical shape extending inwardly in the diametrical direction of the bending tube 94. Further, in peripheral wall portions of the protruding portions 100, opposite openings are formed on the front end side and the rear end side in the direction of the central axis of the bending tube 94 respectively, and these openings form the wire insertion holes 102.

FIGS. 10A to 11C show a fifth embodiment of the present invention. The same reference numerals are assigned to the components having functions similar to those in the fourth embodiment, and these components are not described.

Figure 10A:
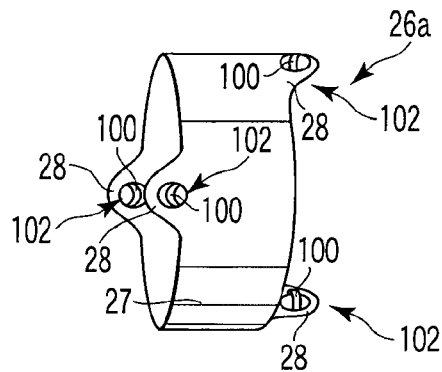
FIG. 10A is a perspective view showing a first bending part of a bending tube of an endoscope in a fifth embodiment of the present invention.
Figure 10B:
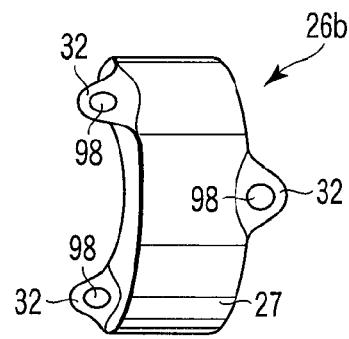
FIG. 10B is a perspective view showing a second bending part of the bending tube of the endoscope in the fifth embodiment of the present invention.
Figure 10C:
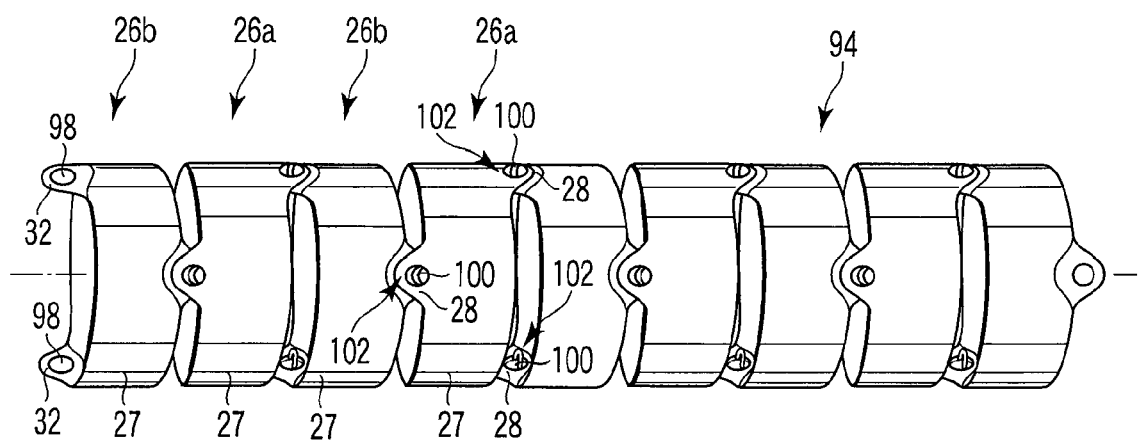
FIG. 10C is a perspective view showing the bending tube of the endoscope in the fifth embodiment of the present invention.

Referring to FIGS. 10A to 10C, a plurality of thin and cylindrical bending parts 26a and 26b of two kinds are coaxially and alternately coupled to each other and arranged side by side in the bending tube 94 forming the framework of the bending portion 16 (see FIG. 1).

Furthermore, on one end face of the circumferential portion 27 of the first bending part 26a, the first pair of protruding portion tongue piece portions 28 is provided at positions symmetrical with respect to the central axis of the bending tube 94. On the other end face of the first bending part 26a, the second pair of protruding portion tongue piece portions 28 is disposed at such positions that the first pair of protruding portion tongue piece portions 28 is rotationally moved about 90° when viewed in the direction of the central axis of the bending tube 94. As in the fourth embodiment, the protruding portions 100 are formed in the first and second pairs of protruding portion tongue piece portions 28.

On one end face of the circumferential portion 27 of the second bending part 26b, the first pair of receiving portion tongue piece portions 32 is provided at positions symmetrical with respect to the central axis of the bending tube 94. On the other end face of the second bending part 26b, the second pair of receiving portion tongue piece portions 32 is disposed at such positions that the first pair of receiving portion tongue piece portions 32 is rotationally moved about 90° when viewed in the direction of the central axis of the bending tube 94. Steps corresponding to the thickness of the bending part 26b are formed between the circumferential portion 27 and the first and second pairs of receiving portion tongue piece portions 32. As in the fourth embodiment, the through holes 98 are formed in the first and second pairs of receiving portion tongue piece portions 32.

In the bending tube 94, the first and second bending part 26a and 26b are alternately provided side by side. Further, the protruding portion tongue piece portions 28 of the first bending part 26a and the receiving portion tongue piece portions 32 of the bending part 26b are made to overlap each other, and the protruding portions 100 of the protruding portion tongue piece portions 28 are inserted rotatably in the through holes 98 of the receiving portion tongue piece portions 32.

Next, a method of manufacturing the endoscopic insertion portion 12 in the present embodiment will be described.

In the pressing machine used in the present embodiment, first and second lines perpendicular to each other are used, and the first line joins the second line and then terminates.

A method of manufacturing the bending tube 94 will be described in detail for each separate step in each line with reference to FIG. 11A to FIG. 11C.

First Line

Step 1 (First Processing Position PA1)

Figure 11A:
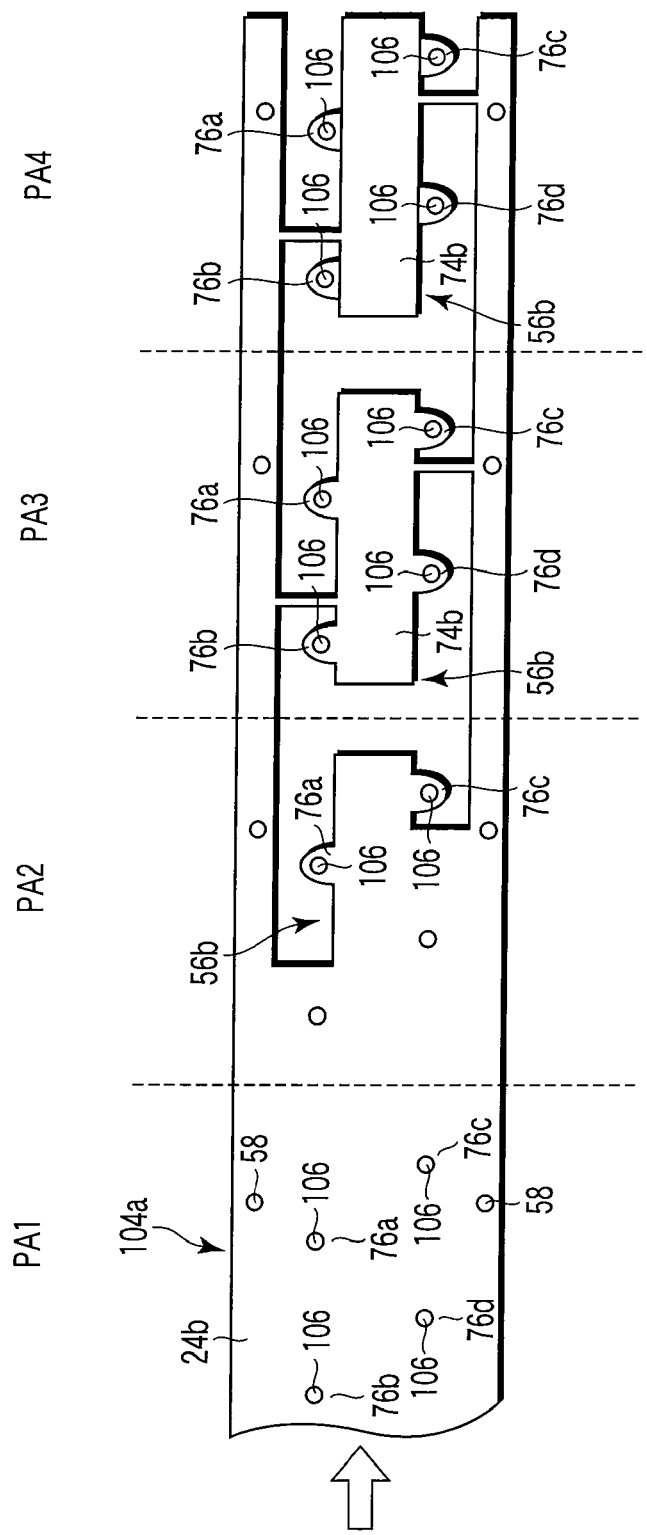
FIG. 11A is a first diagram for explaining the press processing of a plate material in a method of manufacturing the endoscopic insertion portion in the fifth embodiment of the present invention.

As shown in FIG. 11A, the pilot holes 58 are formed at both ends in the width direction of a second plate material 24b. Further, in a certain second plate-shaped portion 104b of the second plate material 24b, the through hole preparation portions 106 serving as preparation holes for forming the through holes 98 of the receiving portion tongue piece portions 32 are formed by punching processing in the first and second pairs of receiving portion tongue piece portion preparation portions 76a, 76b, 76c and 76d for forming the first and second pairs of receiving portion tongue piece portions 32 of the second bending part 26b.

The first pair of receiving portion tongue piece portion preparation portions 76a and 76b is provided side by side in the longitudinal direction of the second plate material 24b, and the second pair of receiving portion tongue piece portion preparation portions 76c and 76d is also provided side by side in the longitudinal direction of the second plate material 24b. The receiving portion tongue piece portion preparation portion 76d which is one of the second pair of receiving portion tongue piece portion preparation portions 76c and 76d is disposed at a position substantially in the middle of the first pair of receiving portion tongue piece portion preparation portions 76a and 76b with respect to the longitudinal direction of the second plate material 24b. Here, the length between the first pair of receiving portion tongue piece portion preparation portions 76a and 76b (the length between the second pair of receiving portion tongue piece portion preparation portions 76c and 76d) in the longitudinal direction of the second plate material 24b corresponds to the length between the first pair of receiving portion tongue piece portions 32 (the length between the second pair of receiving portion tongue piece portions 32) in the circumferential direction of the second bending part 26b. The length between the first pair of receiving portion tongue piece portion preparation portions 76a and 76b and the second pair of receiving portion tongue piece portion preparation portions 76c and 76d in the width direction of the second plate material 24b corresponds to the length between the first pair of receiving portion tongue piece portions 32 and the second pair of receiving portion tongue piece portions 32 in the longitudinal direction of the second bending part 26b.

Step 2 (Second Processing Position PA2)

In Step 2 and Step 3, the second bending part preparation portion 56b for forming the second bending part 26b is formed in the second plate-shaped portion 104b by punching processing.

In Step 2, a relatively small portion of a part scheduled for punching processing is punched.

Step 3 (Third Processing Position PA3)

A relatively large residual portion of the part scheduled for punching processing is punched.

The second circumferential portion preparation portion 74b of the second bending part preparation portion 56b formed in this punching processing is a portion to serve as the circumferential portion 27 of the second bending part 26b, and extend in the longitudinal direction of the second plate material 24b. The first and second pairs of receiving portion tongue piece portion preparation portions 76a, 76b, 76c and 76d having the respective through hole preparation portions 106 extend from one and the other sides of the second circumferential portion preparation portion 74b in the width direction of the second plate material 24b.

Step 4 (Fourth Processing Position PA4)

Step bending processing is carried out in connection portions between the second circumferential portion preparation portion 74b and the receiving portion tongue piece portion preparation portions 76a, 76b, 76c and 76d, and steps corresponding to the thickness of the plate of the second bending part 26b are formed, so that the receiving portion tongue piece portion preparation portions 76a, 76b, 76c and 76d protrude and arranged substantially parallel to the circumferential portion preparation portion 74b on the side serving as the inner peripheral surface of the second bending part 26b (the front side of the page bearing the drawing) of the circumferential portion preparation portion 74b.

Second Line

Step 1 (First Processing Position PB1)

Figure 11B:
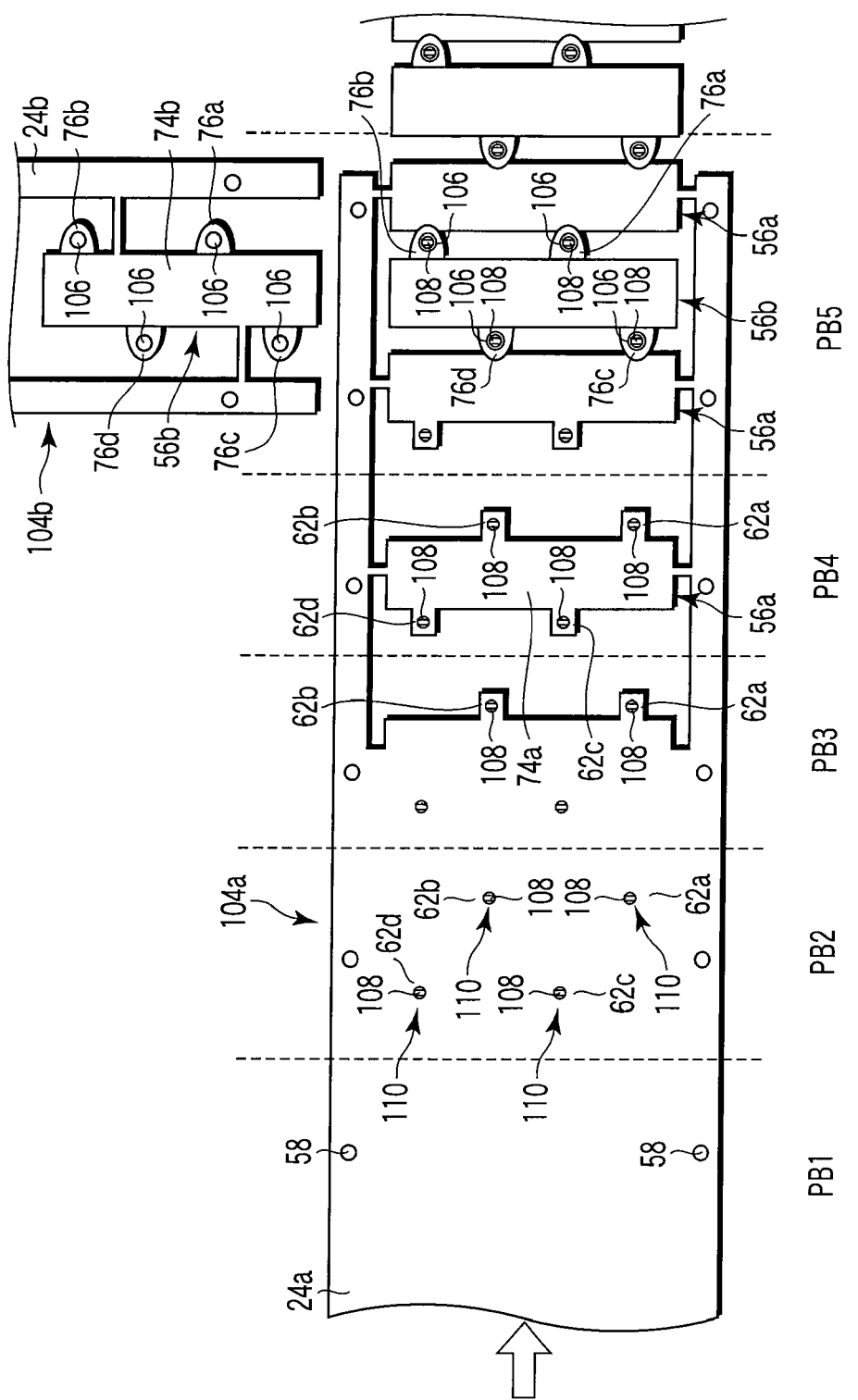
FIG. 11B is a second diagram for explaining the press processing of the plate material in the method of manufacturing the endoscopic insertion portion in the fifth embodiment of the present invention.
Figure 11C:
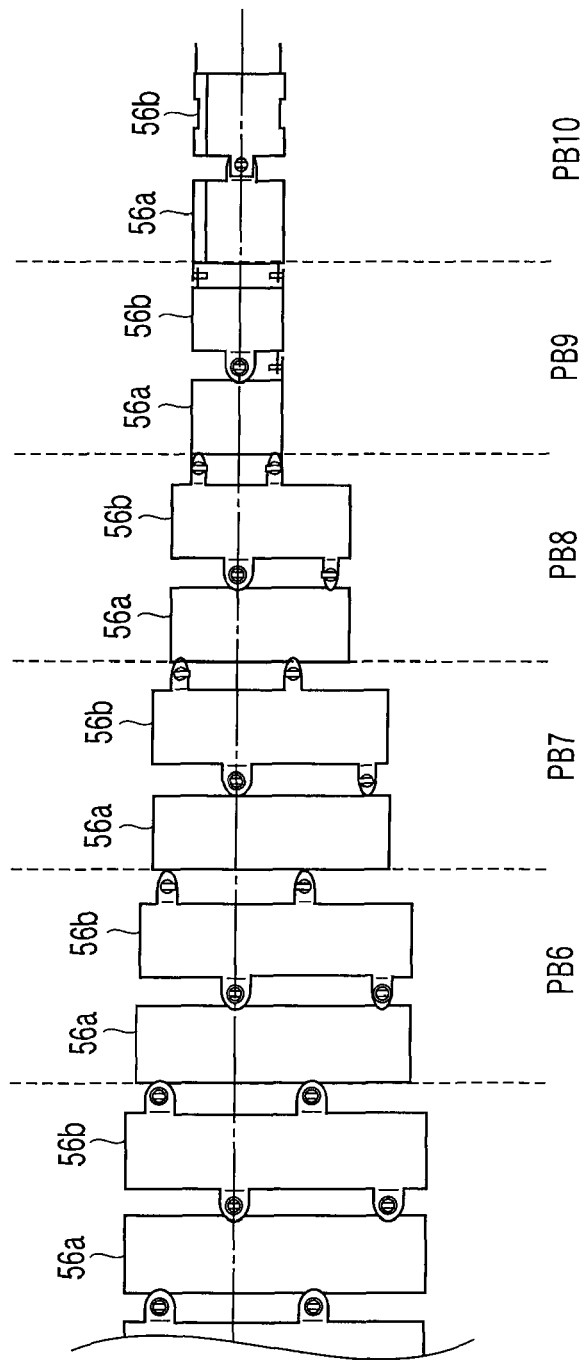
FIG. 11C is a third diagram for explaining the press processing of the plate material in the method of manufacturing the endoscopic insertion portion in the fifth embodiment of the present invention.

As shown in FIG. 11B, the pilot holes 58 are formed at both ends in the width direction of a first plate material 24a.

Step 2 (Second Processing Position PB2)

In a certain first plate-shaped portion 104a of the first plate material 24a, the protruding portion preparation portions 108 for forming the protruding portions 100 of the protruding portion tongue piece portions 28 are formed by press processing in the first and second pairs of protruding portion tongue piece portion preparation portions 62a, 62b, 62c and 62d for forming the first and second pairs of protruding portion tongue piece portions 28 of the first bending part 26a. The form of the protruding portion preparation portions 108 is the same as that in the fourth embodiment. In the protruding portion preparation portions 108, there are formed zonal portions which are formed by drawing processing of press processing and which form convex semicircular shapes from the side serving as the outer peripheral surface of the first bending part 26a to the side serving as the inner peripheral surface thereof (from the rear side to front side of the page bearing the drawing), such that the insertion hole preparation portions 110 are formed.

The first pair of protruding portion tongue piece portion preparation portions 62a and 62b is provided side by side in the width direction of the first plate material 24a, and the second pair of protruding portion tongue piece portion preparation portions 62c and 62d is provided side by side in the width direction of the first plate material 24a in the rear of the first pair of protruding portion tongue piece portion preparation portions 62a and 62b. The protruding portion tongue piece portion preparation portions 62c which is one of the second pair of protruding portion tongue piece portion preparation portions 62c and 62d is disposed at a position substantially in the middle of the first pair of protruding portion tongue piece portion preparation portions 62a and 62b with respect to the width direction of the first plate material 24a. Here, the length between the first pair of protruding portion tongue piece portion preparation portions 62a and 62b (the length between the second pair of protruding portion tongue piece portion preparation portions 62c and 62d) in the width direction of the first plate material 24a corresponds to the length between the first pair of protruding portion tongue piece portions (the length between the second pair of protruding portion tongue piece portions 28) in the circumferential direction of the first bending part 26a. The length between the first pair of protruding portion tongue piece portion preparation portions 62a and 62b and the second pair of protruding portion tongue piece portion preparation portions 62c and 62d in the longitudinal direction of the first plate material 24a corresponds to the length between the first pair of protruding portion tongue piece portions 28 and the second pair of protruding portion tongue piece portions 28 in the axial direction of the first bending part 26a.

Step 3 (Third Processing Position PB3)

In Step 3 and Step 4, the first bending part preparation portion 56a for forming the first bending part 26a is formed in the first plateshaped portion 104a by punching processing.

In Step 3, a relatively small portion of a part scheduled for punching processing is punched.

Step 4 (Fourth Processing Position PB4)

A relatively large residual portion of the part scheduled for punching processing is punched.

The first circumferential portion preparation portions 74a of the first bending part preparation portion 56a formed in this punching processing is a portion serving to form the circumferential portion 27 of the first bending part 26a, and extend in the width direction of the first plate material 24a. The first and second pairs of protruding portion tongue piece portion preparation portions 62a, 62b, 62c and 62d having the respective protruding portion preparation portions 108 extend from the front end side and the rear end side of the first circumferential portion preparation portions 74a in the longitudinal direction of the first plate material 24a.

Step 5 (Fifth Processing Position PB5)

The second bending part preparation portion 56b formed in the first line is guided between the first bending part preparation portions 56a provided side by side in the front and rear at a fifth processing position PB5 of the second line. Then, in the direction vertical to the first plate material 24a, the through hole preparation portions 106 of the first pair of receiving portion tongue piece portion preparation portions 76a and 76b on the front end side of the second bending part preparation portion 56b are aligned with the protruding portion preparation portions 108 of the second pair of protruding portion tongue piece portion preparation portions 62c and 62d on the rear end side of the first bending part 26a on the front end side, and the through hole preparation portions 106 of the second pair of receiving portion tongue piece portion preparation portions 76c and 76d on the rear end side of the second bending part preparation portion 56b are aligned with the protruding portion preparation portions 108 of the first pair of protruding portion tongue piece portion preparation portions 62a and 62b on the front side of the first bending part 26a on the rear end side.

Then, the second bending part preparation portion 56b is struck down by dropping processing from the side serving as the inner peripheral surface of the first bending part 26a to the side serving as the outer peripheral surface thereof (from the front side to rear side of the page bearing the drawing), such that the second bending part preparation portion 56b is separated from the second plate material 24b. As a result, the protruding portion preparation portions 108 of the two first bending part preparation portions 56a are inserted rotatably in the through hole preparation portions 106 of the second bending part preparation portion 56b, and the second bending part preparation portion 56b is connected to the two first bending part preparation portions 56a. That is, the two first bending part preparation portions 56a in the front and rear are coupled to each other by the second bending part preparation portion 56b.

Step 6 to Step 9 (Sixth to Ninth Processing Positions PB6, PB7, PB8 and PB9)

In Step 6 to Step 9, the first bending part preparation portion 56a is separated from the first plate material 24a, and the first and second bending part preparation portions 56a and 56b as a pair obtained by the separation are gradually bent in a U shape up to a final R (curvature) from the side serving as the outer peripheral surface of the bending part 26 to the side serving as the inner peripheral surface thereof (from the rear side to front side of the page bearing the drawing).

Step 10 (Tenth Processing Position PB10)

The first and second bending part preparation portions 56a and 56b which have been bent in a U shape are further subjected to O-shape bending processing, thereby forming the first and second cylindrical bending parts 26a and 26b. At this point, both end faces of the first and second bending part preparation portions 56a and 56b face and abut against each other.

Step 11

After Step 1 to Step 10, the bending tube 94 is discharged from the pressing machine 47. Then, the abutting portions of the bending parts 26a and 26b is joined by forming the junction 38 by means of the laser welding and others.

Therefore, the present embodiment provides the following advantages.

The bending tube 94 in the present embodiment is formed by the bending parts 26a and 26b of two kinds. A certain bending part 26a has the protruding portions 100 for the through holes 98 of the two bending parts 26b provided side by side on one and the other sides of this bending part 26a. The bending part 26b provided side by side with the certain bending part 26a has the through holes 98 for the protruding portions 100 of the two bending parts 26a provided side by side on one and the other sides of this bending part 26b. Such a bending tube 94 can be formed as follows: when the first and second bending part preparation portions 56a and 56b are connected to each other, the bending part preparation portion 56b which is one of the first and second bending part preparation portions 56a and 56b is separated from the plate material 24b which is one of the first and second plate materials 24a and 24b and is connected to the bending part preparation portions 56a which is the other of the first and second bending part preparation portions 56a and 56b of the plate material 24a which is the other of the first and second plate materials 24a and 24b by inserting the protruding portion preparation portions 108 in the through hole preparation portions 106 rotatably. Thus, the connection of the first and second bending part preparation portions 56a and 56b can be achieved with a reduced number of processing steps.

Furthermore, in the second line, the first plate material 24a is continuously processed by being passed on to the processing positions for carrying out the respective steps in the order described above. In the first line, the second plate material 24b is continuously processed by being passed on to the processing positions for carrying out the respective steps in the order described above. Thus, the efficiency of manufacturing the bending tube 94 is drastically improved.

What is claimed is:

1. A method of manufacturing an endoscopic insertion portion which includes a plurality of bending parts provided side by side with each other, wherein a protruding portion is provided in one of each two adjacent ones of the bending parts, and a receiving portion is provided in the other of each two adjacent ones of the bending parts and into which the protruding portion is inserted rotatably so that each two adjacent ones of the bending parts swing with respect to each other, the method comprising:

forming, in at least one plate material, a first bending part preparation portion for the formation of the one bending part and a second bending part preparation portion for the formation of the other bending part;

connecting the first bending part preparation portion and the second bending part preparation portion by press processing; and forming the connected first and second bending part preparation portions into a cylindrical shape by press processing to form cylindrical bending parts connected with each other swingably.

2. The method of manufacturing an endoscopic insertion portion according to claim 1, wherein the forming of the first bending part preparation portion and the second bending part preparation portion includes:

forming a protruding portion preparation portion for the formation of the protruding portion in the plate material by press processing;

forming a receiving portion preparation portion for the formation of the receiving portion in the plate material by press processing;

forming the first bending part preparation portion having the protruding portion preparation portion in the plate material by punching processing; and forming the second bending part preparation portion having the receiving portion preparation portion in the plate material by punching processing, wherein the connecting the first bending part preparation portion and the second bending part preparation portion by press processing includes:

aligning the protruding portion preparation portion with the receiving portion preparation portion in a direction vertical to the plate material by moving one of the first and second bending part preparation portions by Z-shape bending processing; and inserting the protruding portion preparation portion into the receiving portion preparation portion rotatably by subjecting one of the first and second bending part preparation portions to dropping processing, and wherein the forming the first and second bending part preparation portions into the cylindrical shape by press processing includes:

subjecting the first and second bending part preparation portions to U-shape bending processing at least one time; and subjecting the first and second bending part preparation portions which have undergone the U-shape bending processing to O-shape bending processing to form the first and second bending part preparation portions into the cylindrical shape.

3. The method of manufacturing an endoscopic insertion portion according to claim 2, wherein in order to simultaneously process the first and second bending part preparation portions at processing positions for implementation of the manufacturing method, the plate material is passed on to the processing positions in order of:

the forming the protruding portion preparation portion by press processing;

the forming the receiving portion preparation portion by press processing;

the forming the first bending part preparation portion by punching processing;

the forming the second bending part preparation portion by punching processing;

the aligning;

the inserting;

the subjecting to the U-shape bending processing; and the subjecting to the O-shape bending processing.

4. The method of manufacturing an endoscopic insertion portion according to claim 2, further comprising:

joining both ends of the first and second bending part preparation portions which abut against each other due to the O-shape bending processing.

5. The method of manufacturing an endoscopic insertion portion according to claim 2, wherein the bending part has a wire receiving portion through which a wire is inserted, and the manufacturing method further comprises:

forming a wire receiving portion preparation portion for formation of the wire receiving portion by slit processing and bending processing for the plate material.

6. The method of manufacturing an endoscopic insertion portion according to claim 2, wherein the bending part has a wire receiving portion through which a wire is inserted, and the manufacturing method further comprises:

forming a wire receiving portion preparation portion for formation of the wire receiving portion by punching processing and folding processing for the plate material.

7. The method of manufacturing an endoscopic insertion portion according to claim 1, wherein the receiving portion includes a through hole through which the protruding portion is inserted, and:

wherein the forming the first bending part preparation portion and the second bending part preparation portion includes:

forming a protruding portion preparation portion for the formation of the protruding portion in a first plate-shaped portion by press processing;

forming, in the protruding portion preparation portion by press processing, an insertion hole preparation portion for the formation of an insertion hole through which an operation wire for a bending operation of the endoscopic insertion portion is inserted;

forming a through hole preparation portion for the formation of the through hole in a second plate-shaped portion by press processing;

forming the first bending part preparation portion having the protruding portion preparation portion in the first plate-shaped portion by punching processing; and forming the second bending part preparation portion having the through hole preparation portion in the second plate-shaped portion by punching processing, wherein the connecting the first bending part preparation portion and the second bending part preparation portion by press processing includes:

aligning the protruding portion preparation portion with the through hole preparation portion by relatively moving the first and second bending part preparation portions; and connecting the first and second bending part preparation portions to each other by inserting the protruding portion preparation portion into the through hole preparation portion rotatably, and wherein the forming the first and second bending part preparation portions into the cylindrical shape by press processing includes:

subjecting the first and second bending part preparation portions to U-shape bending processing at least one time; and subjecting the first and second bending part preparation portions which have undergone the U-shape bending processing to O-shape bending processing to form the first and second bending part preparation portions connected to each other into the cylindrical shape.

8. The method of manufacturing an endoscopic insertion portion according to claim 7, wherein:

the first plate-shaped portion and the second plate-shaped portion are parts of a same plate material;

the aligning includes aligning the protruding portion preparation portion with the through hole preparation portion in a direction vertical to the plate material by moving one of the first and second bending part preparation portions by Z-shape bending processing; and the connecting by the inserting includes connecting the first and second bending part preparation portions to each other by subjecting one of the first and second bending part preparation portions to dropping processing to insert the protruding portion preparation portion into the through hole preparation portion rotatably.

9. The method of manufacturing an endoscopic insertion portion according to claim 8, wherein in order to simultaneously process the first and second bending part preparation portions at processing positions for implementation of the manufacturing method, the plate material is passed on to the processing positions in order of:

the forming the protruding portion preparation portion by press processing;

the forming the insertion hole preparation portion by press processing;

the forming the through hole preparation portion by press processing;

the forming the first bending part preparation portion by punching processing;

the forming the second bending part preparation portion by punching processing;

the aligning;

the connecting by the inserting;

the subjecting to the U-shape bending processing; and the subjecting to the O-shape bending processing.

10. The method of manufacturing an endoscopic insertion portion according to claim 7, wherein:

the first plate-shaped portion and the second plate-shaped portion are a part of a first plate material and a part of a second plate material, respectively, and the connecting includes connecting one of the first and second bending part preparation portions of one of the first and second plate materials to the other of the first and second bending part preparation portions of the other of the first and second plate materials by separating the one of the first and second bending part preparation portions from the one of the first and second plate materials and then inserting the protruding portion preparation portion into the through hole preparation portion rotatably.

11. The method of manufacturing an endoscopic insertion portion according to claim 10, wherein the first plate material is continuously processed by being passed on to processing positions for implementation of the manufacturing method in order of:

the forming the protruding portion preparation portion by press processing; and the forming the first bending part preparation portion by punching processing, wherein the second plate material is continuously processed by being passed on to processing positions for implementation of the manufacturing method in order of:

the forming the through hole preparation portion by press processing; and the forming the second bending part preparation portion by punching processing, and wherein the first or second plate material is continuously processed by being passed on to processing positions for implementation of the manufacturing method in order of:

the subjecting to the U-shape bending processing; and the subjecting to the O-shape bending processing.

12. The method of manufacturing an endoscopic insertion portion according to claim 3, further comprising:

joining both ends of the first and second bending part preparation portions which abut against each other due to the O-shape bending processing.

* * * * *